US009804138B2

(12) United States Patent
Brown et al.

(10) Patent No.: US 9,804,138 B2
(45) Date of Patent: Oct. 31, 2017

(54) MEASUREMENT OF TOTAL REACTIVE NITROGEN, $NO_y$, TOGETHER WITH $NO_2$, NO, AND $O_3$ VIA CAVITY RING-DOWN SPECTROSCOPY

(71) Applicant: The United States of America, as represented by the Secretary of Commerce, Washington, DC (US)

(72) Inventors: Steven S. Brown, Boulder, CO (US); William P. Dubé, Wheat Ridge, CO (US); Robert J. Wild, Boulder, CO (US)

(73) Assignee: The United States of America, Washington, DC (US)

( * ) Notice: Subject to any disclaimer, the term of this patent is extended or adjusted under 35 U.S.C. 154(b) by 0 days.

(21) Appl. No.: 14/722,214

(22) Filed: May 27, 2015

(65) Prior Publication Data

US 2015/0377850 A1    Dec. 31, 2015

Related U.S. Application Data

(60) Provisional application No. 62/017,298, filed on Jun. 26, 2014.

(51) Int. Cl.
    *G01N 33/00* (2006.01)
(52) U.S. Cl.
    CPC ..... *G01N 33/0037* (2013.01); *G01N 33/0016* (2013.01)
(58) Field of Classification Search
    CPC .................................................. G01N 33/00
    (Continued)

(56) References Cited

U.S. PATENT DOCUMENTS 3,730,686 A * 5/1973 Breitenbach ......... G01N 21/766
                                                      423/213.2
3,877,875 A * 4/1975 Jones .................. G01N 31/005
                                                         422/80
(Continued)

FOREIGN PATENT DOCUMENTS

WO         2006114766        11/2006

OTHER PUBLICATIONS

Singh, T. et al, Journal of the Air Pollution Control Association 1968, 18, 102-105.*

(Continued)

*Primary Examiner* — Arlen Soderquist
(74) *Attorney, Agent, or Firm* — Robert Platt Bell

(57) ABSTRACT

A sensitive, compact detector measures total reactive nitrogen ($NO_y$), as well as $NO_2$, NO, and $O_3$. In all channels, $NO_2$ is directly detected by laser diode based cavity ring-down spectroscopy (CRDS) at 405 nm. Ambient $O_3$ is converted to $NO_2$ in excess NO for the $O_3$ measurement channel. Likewise, ambient NO is converted to $NO_2$ in excess $O_3$. Ambient $NO_y$ is thermally dissociated at 700 C to form $NO_2$ or NO in a heated quartz inlet. Any NO present in ambient air or formed from thermal dissociation of other reactive nitrogen compounds is converted to $NO_2$ in excess $O_3$ after the thermal converter. The precision and accuracy of this instrument make it a versatile alternative to standard chemiluminescence-based $NO_y$ instruments.

14 Claims, 9 Drawing Sheets

(58) Field of Classification Search
USPC .............. 422/52, 83, 91; 436/116–118, 164, 436/171–172
See application file for complete search history.

(56) References Cited

U.S. PATENT DOCUMENTS

| | | | |
|---|---|---|---|
| 3,967,933 | A | 7/1976 | Etess et al. |
| 4,018,562 | A | 4/1977 | Parks et al. |
| 4,066,409 | A | 1/1978 | Fine |
| 4,717,675 | A | 1/1988 | Sievers et al. |
| 4,822,564 | A | 4/1989 | Howard |
| 5,633,170 | A * | 5/1997 | Neti .................. G01N 21/766 423/239.1 |
| 5,807,750 | A * | 9/1998 | Baum ................. G01N 21/31 250/341.1 |
| 5,818,598 | A | 10/1998 | Kebabian |
| 6,207,460 | B1 * | 3/2001 | Kishkovich ......... G01N 33/0006 422/116 |
| 6,296,806 | B1 * | 10/2001 | Kishkovich ........... G01N 21/76 422/52 |
| 6,346,419 | B1 | 2/2002 | Ryerson et al. |
| 6,635,415 | B1 * | 10/2003 | Bollinger ............. G01N 21/766 422/81 |
| 6,791,689 | B1 * | 9/2004 | Weckstrom ............... G01J 3/10 356/437 |
| 6,855,557 | B2 * | 2/2005 | Kishkovich ......... G01N 33/0006 422/62 |
| 7,029,920 | B2 * | 4/2006 | Lanier .................. G01N 1/2258 422/62 |
| 7,045,359 | B2 | 5/2006 | Birks et al. |
| 7,297,549 | B2 * | 11/2007 | Lanier .................. G01N 1/2258 422/62 |
| 7,301,639 | B1 | 11/2007 | Jung et al. |
| 7,323,343 | B2 * | 1/2008 | Cox ..................... G01N 27/123 422/52 |
| 7,704,214 | B2 * | 4/2010 | Abraham-Fuchs ........................ G01N 27/4143 422/84 |
| 8,174,691 | B1 | 5/2012 | Horton et al. |
| 8,654,334 | B1 | 2/2014 | Gupta et al. |
| 8,846,407 | B2 | 9/2014 | Hargrove |
| 2001/0007772 | A1 * | 7/2001 | Li ........................ B24B 37/013 436/113 |
| 2001/0042843 | A1 * | 11/2001 | Cox .................... G01N 27/123 250/504 R |
| 2003/0082821 | A1 * | 5/2003 | Lanier .................. G01N 1/2258 436/118 |
| 2005/0274899 | A1 * | 12/2005 | Butler .................... G01N 21/33 250/373 |
| 2006/0039826 | A1 * | 2/2006 | Nakatani ............ G01N 33/0037 422/68.1 |
| 2006/0108221 | A1 * | 5/2006 | Goodwin ........... G01N 33/0009 204/424 |
| 2006/0236752 | A1 * | 10/2006 | Nakamura ......... G01N 33/0032 73/23.21 |
| 2009/0120212 | A1 | 5/2009 | Hargrove |
| 2009/0137055 | A1 * | 5/2009 | Bognar .............. G01N 33/0037 436/118 |
| 2009/0273785 | A1 * | 11/2009 | Gundersen ........... G01N 21/532 356/437 |
| 2011/0027899 | A1 | 2/2011 | Hargrove et al. |
| 2012/0002212 | A1 | 1/2012 | Chandler et al. |
| 2012/0113426 | A1 | 5/2012 | Rao et al. |
| 2013/0017618 | A1 | 1/2013 | Hargrove et al. |

OTHER PUBLICATIONS

Fahey, D. W. et al, Journal of Atmospheric Chemistry 1985, 3, 435-468.*
Ziereis, H. et al, Journal of Geophysical Research 2000, 105, 3653-3664.*
McClenny, W. A. et al, EPA Report 600R01005, 2000, 85 pages.*
Szabo, N. F. et al, Sensors and Actuators B 2003, 88, 168-177.*
Farmer, D. K. et al, Atmospheric Chemistry and Physics 2006, 6, 3471-3486.*
Hargrove, J. et al, Review of Scientific Instruments 2008, 79, 046109, 3 pages.*
Paul, D. et al, Review of Scientific Instruments 2009, 80, 114101, 8 pages.*
Paul, D. et al, Analytical Chemistry 2010, 82, 6695-6703.*
Wild, R. J. et al, Environmental Science & Technology 2014, 48, 9609-9615.*
Kelly, T. J. et al, Journal of Geophysical Research 1980, 85, 7417-7425.*
Brown, S. S. et al, Journal of Geophysical Research 2003, 108, D9, 4299, 11 pages.*
Fuchs, H. et al, Analytical Chemistry 2008, 80, 6010-6017.*
Fahey, D. W. et al, Journal of Geophysical Research 1986, 91, 9781-9793.*
Olszyna, K. J. et al, Journal of Geophysical Research 1994, 99, 14557-14563.*
Haste, D. R. et al, Atmospheric Environment 1996, 30, 2157-2165.*
Nunnermacker, L. J. et al, Journal of Geophysical Research 1998, 103, 29129-28148.*
Pollack, I. B. et al, Journal of Geophysical Research 2012, 117, D00V05, 14 pages.*
Brown, S. S. et al, Journal of Geophysical Research: Atmospheres 2013, 118, 8067-8085.*
Day, et al., "A thermal disassociation laser-induced fluorescent instrument for in situ detection of NO2, peroxy nitrates, alkyl nitrates and HN03" Journal of Geophysical Research, Mar. 21, 2002, vol. 107 No. D4.
PCT Search Report PCT/US2015/032535, published Aug. 19, 2015.
Williams, E. J.; Baumann, K.; Roberts, J. M.; Bertman, S. B.; Norton, R. B.; Fehsenfeld, F. C.; Springston, S. R.; Nunnermacker, L. J.; Newman, L.; Olszyna, K.; Meagher, J.; Hartsell, B.; Edgerton, E.; Pearson, J. R.; Rodgers, M. O. Intercomparison of ground-based NOy Measurement techniques. Journal of Geophysical Research: Atmospheres 1998, 103, 22261-22280.
Crosley, D. R. NOy Blue Ribbon panel. Journal of Geophysical Research: Atmospheres 1996, 101, 2049-2052.
Kliner, D. A. V.; Daube, B. C.; Burley, J. D.; Wofsy, S. C. Laboratory investigation of the catalytic reduction technique for measurement of atmospheric NOy. Journal of Geophysical Research: Atmospheres 1997, 102, 10759-10776.
Neuman, J. A.; Huey, L. G.; Ryerson, T. B.; Fahey, D. W. Study of Inlet Materials for Sampling Atmospheric Nitric Acid. Environmental Science & Technology 1999, 33, 1133-1136.
Dubé, W. P.; Brown, S. S.; Osthoff, H. D.; Nunley, M. R.; Ciciora, S. J.; Paris, M. W.; McLaughlin, R. J.; Ravishankara, A. R. Aircraft instrument for simultaneous, in situ measurement of NO3 and N2O5 via pulsed cavity ring-down spectroscopy. Review of Scientific Instruments 2006, 77.
Wooldridge, P. J.; Perring, A. E.; Bertram, T. H.; Flocke, F. M.; Roberts, J. M.; Singh, H. B.; Huey, L. G.; Thornton, J. A.; Wolfe, G. M.; Murphy, J. G.; Fry, J. L.; Rollins, A. W.; LaFranchi, B. W.; Cohen, R. C. Total Peroxy Nitrates in the atmosphere: the Thermal Dissociation-Laser Induced Fluorescence (TD-LIF) technique and comparisons to speciated PAN measurements. Atmospheric Measurement Techniques 2010, 3, 593-607.
Di Carlo, P.; Aruffo, E.; Busilacchio, M.; Giammaria, F.; Dari-Salisburgo, C.; Biancofiore, F.; Visconti, G.; Lee, J.; Moller, S.; Reeves, C. E.; Bauguitte, S.; Forster, G.; Jones, R. L.; Ouyang, B. Aircraft based four-channel thermal dissociation laser induced fluorescence instrument for simultaneous measurements of NO2, total peroxy nitrate, total alkyl nitrate, and HNO3. Atmospheric Measurement Techniques 2013, 6, 971-980.
Pérez, I. M.; Wooldridge, P. J.; Cohen, R. C. Laboratory evaluation of a novel thermal dissociation chemiluminescence method for in situ detection of nitrous acid. Atmospheric Environment 2007, 41, 3993-4001.
Thaler, R. D.; Mielke, L. H.; Osthoff, H. D. Quantification of Nitryl Chloride at Part Per Trillion Mixing Ratios by Thermal Dissociation Cavity Ring-Down Spectroscopy. Analytical Chemistry 2011, 83, 2761-2766.

(56) References Cited

OTHER PUBLICATIONS

Mazurenka, M. I.; Fawcett, B. L; Elks, J. M.; Shallcross, D. E.; Orr-Ewing, A. J. 410-nm diode laser cavity ring-down spectroscopy for trace detection of NO2. Chemical Physics Letters 2003, 367, 1-9.

Wada, R.; Orr-Ewing, A. J. Continuous wave cavity ring-down spectroscopy measurement of NO2 mixing ratios in ambient air. Analyst 2005, 130, 1595-1600.

Hargrove, J.; Wang, L.; Muyskens, K.; Muyskens, M.; Medina, D.; Zaide, S.; Zhang, J. Cavity Ring-Down Spectroscopy of Ambient NO2 with Quantification and Elimination of Interferences. Environmental Science & Technology 2006, 40, 7868-7873.

Castellanos, P.; Luke, W. T.; Kelley, P.; Stehr, J. W.; Ehrman, S. H.; Dickerson, R. R. Modification of a commercial cavity ring-down spectroscopy NO2 detector for enhanced sensitivity. Review of Scientific Instruments 2009, 80.

Fuchs, H.; Dubé, W. P.; Lerner, B. M.; Wagner, N. L.; Williams, E. J.; Brown, S. S. A Sensitive and Versatile Detector for Atmospheric NO2 and NOx Based on Blue Diode Laser Cavity Ring-Down Spectroscopy. Environmental Science & Technology 2009, 43, 7831-7836, PMID: 19921901.

Washenfelder, R. A.; Wagner, N. L.; Dubé, W. P.; Brown, S. S. Measurement of Atmospheric Ozone by Cavity Ring-down Spectroscopy. Environmental Science & Technology 2011, 45, 2938-2944.

Wagner, N. L.; Dubé, W. P.; Washenfelder, R. A.; Young, C. J.; Pollack, I. B.; Ryerson, T. B.; Brown, S. S. Diode laser-based cavity ring-down instrument for NO3, N2O5, NO, NO2 and O3 from aircraft. Atmospheric Measurement Techniques 2011, 4, 1227-1240.

Rollins, A. W.; Smith, J. D.; Wilson, K. R.; Cohen, R. C. Real Time In Situ Detection of Organic Nitrates in Atmospheric Aerosols. Environmental Science & Technology 2010, 44, 5540-5545.

Johnston, H. S.; Cantrell, C. A.; Calvert, J. G. Unimolecular decomposition of NO3 to form NO and O2 and a review of N2O5/NO3 kinetics. Journal of Geophysical Research: Atmospheres 1986, 91, 5159-5172.

Reisen, F.; Arey, J. Atmospheric Reactions Influence Seasonal PAH and Nitro-PAH Concentrations in the Los Angeles Basin. Environmental Science & Technology 2005, 39, 64-73.

Axson, J. L.; Washenfelder, R. A.; Kahan, T. F.; Young, C. J.; Vaida, V.; Brown, S. S. Absolute ozone absorption cross section in the Huggins Chappuis minimum (350-470 nm) at 296 K. Atmospheric Chemistry and Physics 2011, 11, 11581-11590.

Slusher, D. L.; Huey, L. G.; Tanner, D. J.; Flocke, F. M.; Roberts, J. M. A thermal dissociation-chemical ionization mass spectrometry (TD-CIMS) technique for the simultaneous measurement of peroxyacyl nitrates and dinitrogen pentoxide. Journal of Geophysical Research: Atmospheres 2004, 109.

Roberts, J. M.; Veres, P.; Warneke, C.; Neuman, J. A.; Washenfelder, R. A.; Brown, S. S.; Baasandorj, M.; Burkholder, J. B.; Burling, I. R.; Johnson, T. J.; Yokelson, R. J.; de Gouw, J. Measurement of HONO, HNCO, and other inorganic acids by negative-ion proton-transfer chemical-ionization mass spectrometry (NI-PT-CIMS): application to biomas.

Helmig, D.; Thompson, C. R.; Evans, J.; Boylan, P.; Hueber, J.; Park, J.-H. Highly Elevated Atmospheric Levels of Volatile Organic Compounds in the Uintah Basin, Utah. Environmental Science & Technology 2014, in press.

Thermo Electron Corporation Model 43C-TLE Enhanced Trace Level SO2 Analyzer http://www.thermo.com.cn/Resources/200802/productPDF_20982.pdf.

Fact Sheet for NOy Monitoring, Version 3.0 Sep. 28, 2005, Enviromental Protection Agency, http://www.epa.gov/ttnamti1/files/ambient/pm25/spec/noysum2.pdf.

McClenny, W. A., et al., Preparing to measure the effects of the NOx SIP Call Methods for ambient air monitoring of NO, NO2, NOy, and individual NOz species, Journal of the Air & Waste Management Association 2002, 52, 542-562.

\* cited by examiner

MEASUREMENT OF TOTAL REACTIVE NITROGEN, $NO_y$, TOGETHER WITH $NO_2$, NO, AND $O_3$ VIA CAVITY RING-DOWN SPECTROSCOPY

CROSS-REFERENCE TO RELATED APPLICATIONS

The present application claims priority from Provisional U.S. Patent Application No. 62/017,298 filed on Jun. 26, 2014, and incorporated herein by reference.

STATEMENT OF GOVERNMENT INTEREST

The research that led to the development of the present invention was sponsored by the National Oceanic and Atmospheric Administration's (NOAA's) Chemical Sciences Division, Earth System Research Laboratory. NOAA is a part of the U.S. Department of Commerce, a component of the U.S. Federal government. The United States Government has certain rights in this invention.

FIELD OF THE INVENTION

The present invention relates to a new method and apparatus for detection of $NO_y$ as part of a compact system that measures NO, $NO_2$, $NO_y$ and $O_3$ based on Cavity Ring-Down Spectroscopy (CRDS).

BACKGROUND OF THE INVENTION

Measurement of oxides of nitrogen is important in studying air pollution and its effects on the atmosphere. Combustion processes, such as from coal-fired power plants, automobiles, and the like, may produce oxides of nitrogen as a byproduct, typically as NO. In the atmosphere, NO may react with other chemicals, notably ozone ($O_3$) to produce $NO_2$. Combined, $NO_2$ and NO may be referred to as "Nitrogen Oxides" or $NO_x$. Nitrogen Oxides may combine with other chemicals in the atmosphere to produce other nitrogen compounds, which may be referred to as reactive nitrogen or $NO_y$. Studying the effect of $NO_y$ on the atmosphere as well as its concentration levels, as well as ozone ($O_3$) levels requires an instrument or instruments to measure the level of these chemicals in the atmosphere.

Reactive nitrogen compounds play a central role in atmospheric chemistry. Nitrogen oxides ($NO_x \equiv NO + NO_2$) strongly affect the oxidative capacity of the atmosphere through the catalytic cycle that produces ozone ($O_3$) in the lower atmosphere. Total reactive nitrogen ($NO_y$) includes $NO_x$ and all its reservoirs:

$NO_y = NO + NO_2 + NO_3 + 2N_2O_5 + HNO_3 + HONO + HO_2NO_2 + PAN$ (peroxy acetyl nitrates)+aerosol nitrates+organic nitrates+ . . .

Reactive nitrogen compounds ($NO_y$) have been identified as precursors for both ozone and fine particulate matter ($PM_{2.5}$). The EPA's National Ambient Air Monitoring Strategy (NAAMS) calls for deployment of $NO_y$ monitors at approximately 75 locations. The EPA Office of Air Quality Planning and Standards (OAQPS) began an effort to gain knowledge and experience with $NO_y$ monitoring in order to resolve a number of technical issues that have been identified with $NO_y$ monitoring, as well as to be prepared to provide support to State and Local monitoring agencies as they begin to purchase, install, and operate $NO_y$ monitors. (See, e.g., McClenny, W. A., et al., *Preparing to measure the effects of the $NO_x$ SIP Call—Methods for ambient air monitoring of NO, $NO_2$, $NO_y$, and individual $NO_z$ species*, Journal of the Air & Waste Management Association 2002, 52, 542-562, incorporated herein by reference).

$NO_y$ consists of all oxides of nitrogen in which the oxidation state of the N atom is +2 or greater, i.e., the sum of all reactive nitrogen oxides including $NO_x$ ($NO + NO_2$) and other nitrogen oxides referred to as $NO_z$. The major components of $NO_z$ include nitrous acids [nitric acid ($HNO_3$), and nitrous acid (HONO)], peroxy nitrates [peroxyl acetyl nitrate (PAN), methyl peroxyl acetyl nitrate (MPAN), and peroxyl propionyl nitrate, (PPN)], organic nitrates [alkyl nitrates of one or more carbon atoms and multi-functional nitrate species], and particulate nitrates.

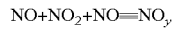

One Prior Art method of measuring $NO_y$ is the use of a thermal catalytic converter to convert reactive nitrogen species to NO followed by detection of NO by its chemiluminescence reaction with an excess of $O_3$. NO is measured by bypassing the converter. The combination of $NO_2$ and $NO_z$ can be then determined by the difference. This procedure is similar to the Prior Art methodology used to measure $NO_x$, however, the catalytic converter temperature is higher in order to more completely convert $NO_z$ species, and the converter has been moved to very near the sample inlet to avoid line losses of "sticky" $NO_y$ species such as $HNO_3$.

The $NO_x$ measurement produced by this method is not considered accurate by the research community, although it is still currently used by the regulatory community. This converter operates through reduction of $NO_y$ to NO in a heated molybdenum catalyst. When the molybdenum catalyst is operated at somewhat lower temperature, the measurement is interpreted as being $NO_x$ and not $NO_y$ (i.e., only the $NO_2$ is supposedly converted to NO at the lower temperature). The $NO_y$ measurement may be acceptable if the heated molybdenum converter is placed very close to the end of the inlet, but the $NO_x$ measurement generally includes some fraction of the $NO_y$ compounds and is therefore considered only an upper limit to the actual $NO_x$.

Knowledge of the abundance of this chemical family, as well as NO, $NO_2$, and the related compound $O_3$, is a useful indicator of total nitrogen emissions, air mass age, competition between different chemical processes, and the efficiency of ozone production associated with particular emission sources. Again, standard measurements of $NO_y$ rely on catalytic decomposition of $NO_y$ to NO, followed by NO detection using chemiluminescence (See, e.g., Fahey, D. et al., *Evaluation of a catalytic reduction technique for the measurement of total reactive odd-nitrogen $NO_y$ in the atmosphere*, Journal of Atmospheric Chemistry 1985, 3, 435-468, incorporated herein by reference).

The most commonly used materials for conversion are gold and molybdenum. However, catalytic converters are prone to deterioration, affecting conversion efficiencies. As a result, they require frequent calibrations and need to be "reconditioned" or cleaned periodically, depending on the history of exposure (See, e.g., Crosley, D. R., *$NO_y$ Blue Ribbon panel*. Journal of Geophysical Research, Atmospheres 1996, 101, 2049-2052, incorporated herein by reference).

Additionally, the chemical processes involved in the catalytic conversion are not fully understood, as illustrated by Kliner, D. A. V. et al., *Laboratory investigation of the catalytic reduction technique for measurement of atmospheric $NO_y$*, Journal of Geophysical Research: Atmospheres 1997, 102, 10759-10776, also incorporated herein by reference.

Inlet design can also play a major role, as some $NO_y$ species, notably $HNO_3$, can suffer significant losses on inlet surfaces as described by Williams, E. J. et al., *Intercomparison of ground-based $NO_y$ measurement techniques*, Journal of Geophysical Research: Atmospheres 1998, 103, 22261-22280, and Neuman, J. A. et al., *Study of Inlet Materials for Sampling Atmospheric Nitric Acid*, Environmental Science & Technology 1999, 33, 1133-1136, both which are incorporated herein by reference.

Thus it remains a requirement in the art to provide a compact and efficient instrument for measuring $NO_y$, $NO_2$, NO, and $O_3$ concentrations in the atmosphere.

BRIEF SUMMARY OF THE INVENTION

The present invention provides a new method and apparatus for detection of $NO_y$ as part of a compact system that uses four channels to simultaneously measure NO, $NO_2$, $NO_y$ and $O_3$ based on cavity ring-down spectroscopy (CRDS). Similar to direct absorption spectroscopy, CRDS is an absolute measurement of trace gas concentration, with an accuracy limited only by knowledge of the absorption cross section, inlet sampling losses, and potential interfering absorbers.

The instrument has lower power, size, weight, and vacuum requirements than a chemiluminescence-based instrument while approaching its sensitivity, precision and time response. In the $NO_y$ CRDS instrument of the present invention, $NO_y$ and its components are converted into $NO_2$ by thermal decomposition (TD) in a fused silica inlet (henceforth referred to as quartz, following convention), followed by the addition of ozone to convert NO to $NO_2$. $NO_2$ is then measured using a cavity ring-down spectroscopy instrument, utilizing a nominally 405 nm laser. The device may comprise four parallel channels, each driven by the same laser, to measure NO, $NO_2$, $NO_y$ and $O_3$, respectively, such that overall $NO_y$ may be measured, as well as its components NO, $NO_2$, as well as ozone ($O_3$).

The successful use of TD has been demonstrated for various individual $NO_y$ compounds. Dubé, W. P. et al., demonstrated the successful use of TD for $N_2O_5$ in *Aircraft instrument for simultaneous, in situ measurement of $NO_3$ and $N_2O_5$ via pulsed cavity ring-down spectroscopy*, Review of Scientific Instruments 2006, 77, incorporated herein by reference.

The successful use of TD for peroxy nitrates has been demonstrated, for example, by Wooldridge, P. J. et al., *Total Peroxy Nitrates (Σ PNs) in the atmosphere: the Thermal Dissociation-Laser Induced Fluorescence (TD-LIF) technique and comparisons to speciated PAN measurements*, Atmospheric Measurement Techniques 2010, 3, 593-607, and Di Carlo, P.; et al., *Aircraft based four-channel thermal dissociation laser induced fluorescence instrument for simultaneous measurements of $NO_2$, total peroxy nitrate, total alkyl nitrate, and $HNO_3$*. Atmospheric Measurement Techniques 2013, 6, 971-980, both of which are incorporated herein by reference.

The successful use of TD for HONO has been demonstrated by Pérez, I. M.; Wooldridge, P. J.; Cohen, R. C. *Laboratory evaluation of a novel thermal dissociation chemiluminescence method for in situ detection of nitrous acid*, Atmospheric Environment 2007, 41, 3993-4001, incorporated herein by reference.

The successful use of TD for $ClNO_2$ has been demonstrated by Thaler, R. D.; Mielke, L. H.; Osthoff, H. D. *Quantification of Nitryl Chloride at Part Per Trillion Mixing Ratios by Thermal Dissociation Cavity Ring-Down Spectroscopy*, Analytical Chemistry 2011, 83, 2761-2766, incorporated herein by reference.

The successful use of TD for alkyl nitrates and $HNO_3$ has been demonstrated by Day, D. A.; Wooldridge, P. J.; Dillon, M. B.; Thornton, J. A.; Cohen, R. C., *A thermal dissociation laser-induced fluorescence instrument for in situ detection of $NO_2$, peroxy nitrates, alkyl nitrates, and $HNO_3$*, Journal of Geophysical Research: Atmospheres 2002, 107, ACH 4-1-ACH 4-14, incorporated herein by reference.

However, the combination of thermal dissociation and ozone is a new method to determine total $NO_y$. Combined with existing techniques for measuring NO, $NO_2$, and $O_3$, the present invention allows all four of these important and related species to be measured simultaneously in a single four-channel instrument, with precision, accuracy, and time response sufficient for their measurement in ambient air across a range of environments and measurement platforms, including measurements from moving vehicles.

The instrument and method of the present invention, all of the $NO_y$ is converted to $NO_2$ (not NO) using a much hotter oven (quartz at substantially 650° C. to 750° C.) than the Prior Art, with no catalyst. The NO is then converted $NO_2$ using the addition of ozone, and the $NO_2$ measured by cavity ring down spectroscopy. The $NO_y$ and $NO_x$ channels are thus more accurate than the Prior Art techniques (using catalytic converters and chemiluminescence) for measuring $NO_z$. This instrument may be used in a stand-alone mode, or in a four-channel embodiment to measure $O_3$, $NO_x$, $NO_2$, and $NO_y$.

In one preferred embodiment, four channels are provided, to measure $O_3$, $NO_x$, $NO_2$, and $NO_y$ using the same 405 nm laser. All four channels use measurement of $NO_2$ to infer or calculate levels of $O_3$, $NO_y$, $NO_2$, and $NO_y$. The same laser, suitably divided, may be used for all four channels, or separate lasers provided. Using a single laser may be preferable, as the same frequency of light is assured between channels, thus elimination this variation from cross-channel calibration. A single cavity ring-down spectrometer (CRDS), suitably plumbed, may sequentially take measurements for all four channels. In the preferred embodiment, separate cavity ring-down spectrometers are provided for each channel.

The $NO_2$ channel is relatively straightforward. An atmospheric sample is acquired and a "blank volume" is used to provide the same residence time as in the other channels, as the $NO_2$ channel does not use a reactor vessel as with the other channels. This ambient $NO_2$ may then be measured in by a cavity ring-down spectrometer (CRDS). The resultant measurement will be proportional to the amount of ambient $NO_2$ in the atmospheric sample. This value may be used by itself, in atmospheric science studies, but may also be used to determine the baseline amount of ambient $NO_2$ to subtract this value out from other channel data as will be discussed below.

The NO (and $NO_y$) channel reacts an atmospheric sample with a supply of $O_3$ in a reactor vessel. The resultant reaction combines the ambient NO with the $O_3$ in the vessel to form $NO_2$. The resultant sample now has both ambient $NO_2$ along with $NO_2$ converted from NO. Since the amount of NO in the original sample has been converted to a similar amount of $NO_2$, measuring the overall $NO_2$ will provide a measurement of NO along with ambient $NO_2$. This combined sample may then be measured in by a cavity ring-down spectrometer (CRDS). The resultant measurement will be proportional to the amount of NO and ambient $NO_2$ in the atmospheric sample, which yields the value for $NO_x$. Since the amount of ambient $NO_2$ is measured by the $NO_2$ channel, this value can be subtracted out by the data acquisition system, thus yielding a measurement of NO in the atmospheric sample as well.

The $O_3$ channel reacts an atmospheric sample with a supply of NO in a reactor vessel. Note that this is exactly the reverse of how the NO channel operates, where $O_3$ is added to the NO, however the reaction is the same. The resultant reaction combines the ambient $O_3$ in the vessel with NO to form $NO_2$, which then may be measured in by a cavity ring-down spectrometer (CRDS). The resultant measurement will be proportional to the amount of $O_3$ and ambient $NO_2$ in the atmospheric sample. Since the amount of ambient $NO_2$ is measured by the $NO_2$ channel, this value can be subtracted out by the data acquisition system, thus yielding a measurement of $O_3$ in the atmospheric sample.

The $NO_y$ channel first decomposes all reactive nitrogen compounds in the atmospheric sample in a substantially 650° C. to 750° C. quartz oven, as will be described below in more detail. In the oven, the $NO_y$ breaks down into NO and $NO_2$. The sample containing the combined NO and $NO_2$ is then fed into a reactor, where, as in the NO channel, the NO in the sample reacts with a supply of $O_3$ in the reactor vessel. The resultant reaction converts the ambient NO in the vessel to $NO_2$. The amount of NO and $NO_2$ in the decomposed sample will be proportional to the amount of $NO_y$, and since the NO has been converted to a similar amount of $NO_2$, measuring the overall $NO_2$ will provide a measurement of overall $NO_y$. The decomposed and reacted sample may then be measured in by a cavity ring-down spectrometer (CRDS). The resultant measurement will be proportional to the amount of $NO_y$ in the atmospheric sample. Since the amount of ambient $NO_2$ is measured by the $NO_2$ channel and the amount of NO and $NO_x$ is measured by the NO channel, other values, such as $NO_z$ can be calculated ($NO_y$—$NO_x$) by the data acquisition system.

By using the same reaction of $O_3$ and NO, three of the four channels can measure different atmospheric components using the same or similar hardware. With the addition of the heater oven, $NO_y$ can be measured as proportion to the resultant $NO_2$ after decomposition and reaction. Thus, the present invention provides measurement of the four basic compounds of interest to atmospheric scientists ($O_3$, $NO_y$, $NO_2$, and $NO_y$) with improved accuracy, in a robust and compact instrument.

DETAILED DESCRIPTION OF THE INVENTION

Figure 1:
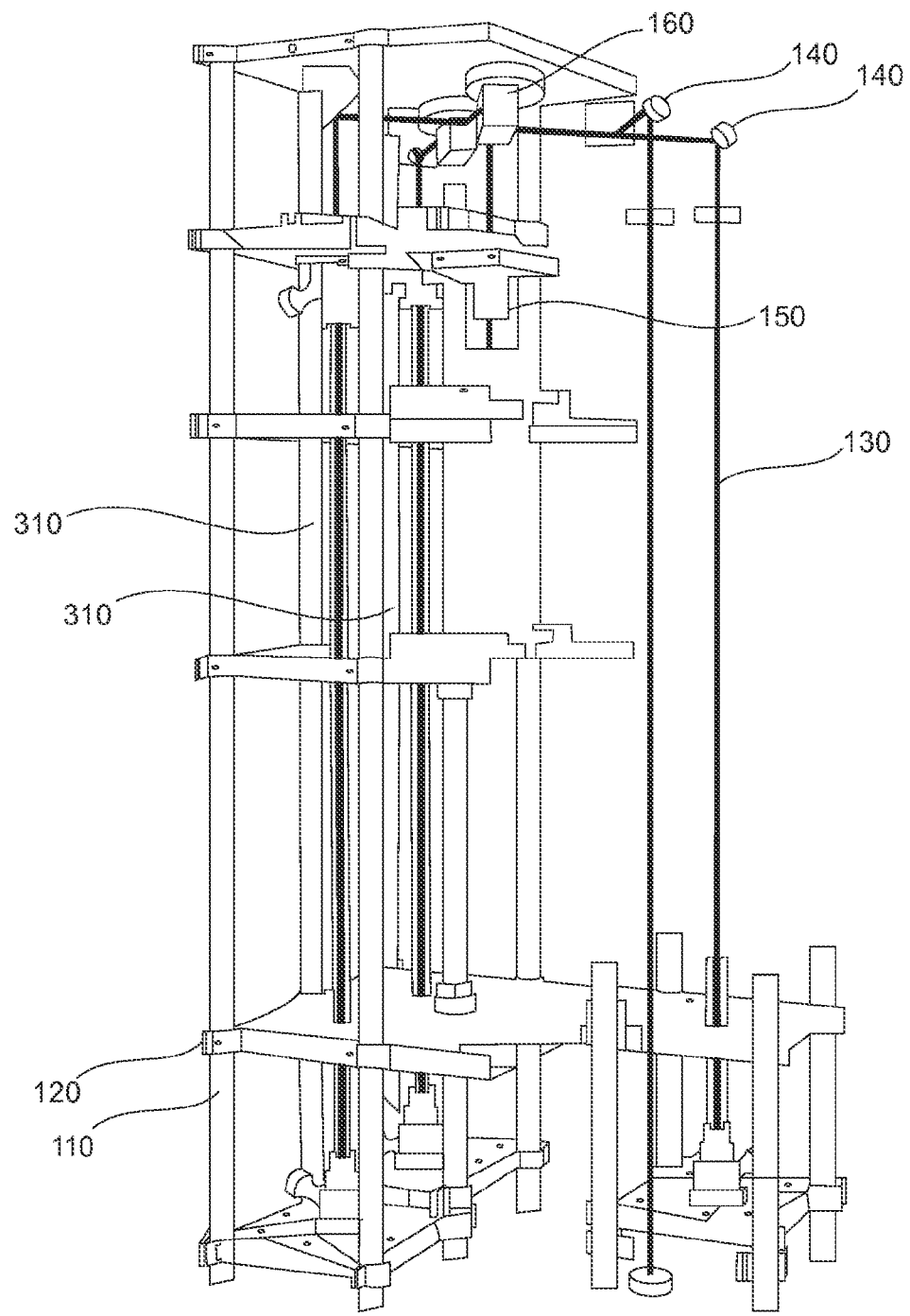
FIG. 1 is a schematic of the custom cage system housing all the optical components.

The instrument of the present invention is based on the detection of $NO_2$ via cavity ring-down spectroscopy. General concepts in cavity ring-down spectroscopy are described in Mazurenka, M. I.; Fawcett, B. L.; Elks, J. M.; Shallcross, D. E.; Orr-Ewing, A. J. *410-nm diode laser cavity ring-down spectroscopy for trace detection of NO*, Chemical Physics Letters 2003, 367, 1-9, Wada, R.; Orr-Ewing, A. J. *Continuous wave cavity ring-down spectroscopy measurement of $NO_2$ mixing ratios in ambient air*, Analyst 2005, 130, 1595-1600, Hargrove, J.; Wang, L.; Muyskens, K.; Muyskens, M.; Medina, D.; Zaide, S.; Zhang, J. *Cavity Ring-Down Spectroscopy of Ambient $NO_2$ with Quantification and Elimination of Interferences*, Environmental Science & Technology 2006, 40, 7868-7873, and Castellanos, P.; Luke, W. T.; Kelley, P.; Stehr, J. W.; Ehrman, S. H.; Dickerson, R. R. *Modification of a commercial cavity ring-down spectroscopy $NO_2$ detector for enhanced sensitivity*, Review of Scientific Instruments 2009, 80, all of which are incorporated herein by reference.

The working principle of CRDS, as well as the conversion of $O_3$ and NO to $NO_2$, has been described in detail, for example by Fuchs, H.; Dubé, W. P.; Lerner, B. M.; Wagner, N. L.; Williams, E. J.; Brown, S. S. *A Sensitive and Versatile Detector for Atmospheric $NO_2$ and $NO_x$ Based on Blue Diode Laser Cavity Ring-Down Spectroscopy*, Environmental Science & Technology 2009, 43, 7831-7836, PMID: 19921901, and Washenfelder, R. A.; Wagner, N. L.; Dubé, W. P.; Brown, S. S. *Measurement of Atmospheric Ozone by Cavity Ring-down Spectroscopy*, Environmental Science & Technology 2011, 45, 2938-2944, both of which are incorporated herein by reference, and will only be summarized here with emphasis on the design improvements. In the present invention, an 80 mW laser diode centered at 405 nm and modulated with a 2 kHz square wave provides light for the four measurement channels.

Cavity Ring-Down Spectroscopy (CRDS) is a highly sensitive optical spectroscopic technique that enables measurement of absolute optical extinction by samples that scatter and absorb light. It has been widely used to study gaseous samples which absorb light at specific wavelengths, and in turn to determine mole fractions down to the parts per trillion level. The technique is also known as Cavity Ring-down Laser Absorption Spectroscopy (CRLAS).

A typical CRDS setup consists of a substantially 405 nm laser that is used to illuminate a high-finesse optical cavity, which in its simplest form consists of two highly reflective mirrors. When the laser is in resonance with a cavity mode, intensity builds up in the cavity due to constructive interference. The laser is then turned off in order to allow the measurement of the exponentially decaying light intensity leaking from the cavity. During this decay, light is reflected back and forth thousands of times between the mirrors giving an effective path length for the extinction on the order of a few kilometers. The frequency of substantially 405 nm was chosen as it is optimized for detecting $NO_2$ in a gas sample. Other frequencies may be used within the spirit and scope of the invention, and indeed, the laser itself may be prone to frequency drift. Periodic zeroing of the apparatus helps compensate for this drift, as well as variations in the output of the photomultiplier tube detector.

If something that absorbs light is placed in the cavity, the amount of light decreases faster—it makes fewer bounces before it is all gone. A CRDS setup measures how long it takes for the light to decay to 1/e of its initial intensity, and this "ringdown time" can be used to calculate the concentration of the absorbing substance in the gas mixture in the cavity.

A Faraday optical isolator provides protection from optical feedback into the laser. When the light is modulated off, the intensity inside the optical cavities decreases exponentially as measured by four photomultiplier tubes (PMT; one for each channel of a four-channel embodiment of the present invention) that detect the light intensity transmitted through the rear mirrors. The exponential decays are co-added and fitted once per second to extract the time constant with ($\tau$) and without ($\tau_0$) the absorber present. The number density of the absorber is then given by:

$$[NO_2] = \frac{1}{c\sigma_{NO_2}}\left(\frac{1}{\tau} - \frac{1}{\tau_0}\right) \quad (1)$$

where c is the speed of light and $\sigma_{NO2}$ is the $NO_2$ absorption cross section. Previous 405 nm CRDS instruments from this group have included purge volumes adjacent to the mirrors to maintain their cleanliness. Purge volumes require a multiplicative factor, RL=d/l in equation 1, where d is the mirror separation and l is the length over which the sample is present. This factor may have had a dependence on pressure that introduces uncertainties into the measurement as described, for example, by Wagner, N. L.; Dubé, W. P.; Washenfelder, R. A.; Young, C. J.; Pollack, I. B.; Ryerson, T. B.; Brown, S. S. *Diode laser-based cavity ring-down instrument for $NO_3$, $N_2O_5$, NO, $NO_2$ and $O_3$ from aircraft*, Atmospheric Measurement Techniques 2011, 4, 1227-1240, incorporated herein by reference. The instrument of the present invention does not currently include mirror purge volumes, which simplifies the calibrations and eliminates a possible source of error. However, such purge volumes could be provided without departing from the spirit and scope of the present invention.

FIG. 1 is a schematic of the custom cage system that houses all the optical components for a four-channel embodiment of the present invention. A large section of the framework has been cut out of the Figure, for ease of illustration. The laser paths 130 are shown in dark lines, and the optical system components have been left in place. The combination of aluminum plates 120 and carbon fiber rods 110 give the system high mechanical rigidity, helping to achieve a measurement precision of a few pptv on a minute timescale.

Referring to FIG. 1, the optical system is mounted in a custom designed cage system with ½ inch carbon fiber rods 110 providing stability against mechanical and thermal stress. A single laser 150 may be used for all four channels of the system. The beam 130 from laser 150, which may comprise a 405 nm laser, may be divided by divider(s) 160 into four separate paths. Mirrors 140 may be used to divert the path of the beam 130 into four parallel paths as illustrated. The beams 130 are then fed into optical cavities 310, of which only two are shown in this cutaway drawing.

The instrument as a whole is compact and requires low power and maintenance. It measures approximately 110 cm high with a 50 by 70 cm footprint, and consumes 300 W of power at its peak. It weighs 95 kg, which includes the sample pump, a zero air generator, and the data acquisition system. The data acquisition system, however, has not been designed for low weight and currently contributes 15 kg, a figure which could be substantially reduced.

The instrument may also require a cylinder (or other source) of 02 (not shown) and a cylinder (or other source) of NO (2000 ppm in Nitrogen) also not illustrated in this Figure. These additions can be contained in 1.2 L cylinders mounted directly in the instrument rack and last for about one week of continuous operation. Standard large cylinders would provide more than 120 days of continuous operation.

In the preferred embodiment, four channels are provided to measure NO, $NO_2$, $NO_y$, and $O_3$. $NO_2$ is directly measured in all channels via equation 1, whereas NO, $O_3$, and $NO_y$ are quantitatively converted to $NO_2$ prior to measurement as will be described in more detail below. Atmospheric NO is converted to $NO_2$ via reaction with excess $O_3$, created by flowing $O_2$ over a Hg Pen-Ray® Model 3SC-9 lamp (185 nm) from UVP, LLC of Upland California.

As described in detail by Fuchs et al., cited above, the added $O_3$ results in a small percentage (<1%) of $NO_2$ conversion to $NO_3$, which subsequently reacts with $NO_2$ to form $N_2O_5$. Similarly, $O_3$ is converted to $NO_2$ via the same reaction by addition of excess NO as described by Washenfelder et al., cited above, but without the $N_2O_5$ interference because $NO+NO_3 \rightarrow 2NO_2$. Conversion of the $NO_y$ species is performed via gas-phase thermal dissociation in a quartz inlet, chosen for its high melting point and because it is relatively unreactive.

Figure 2:
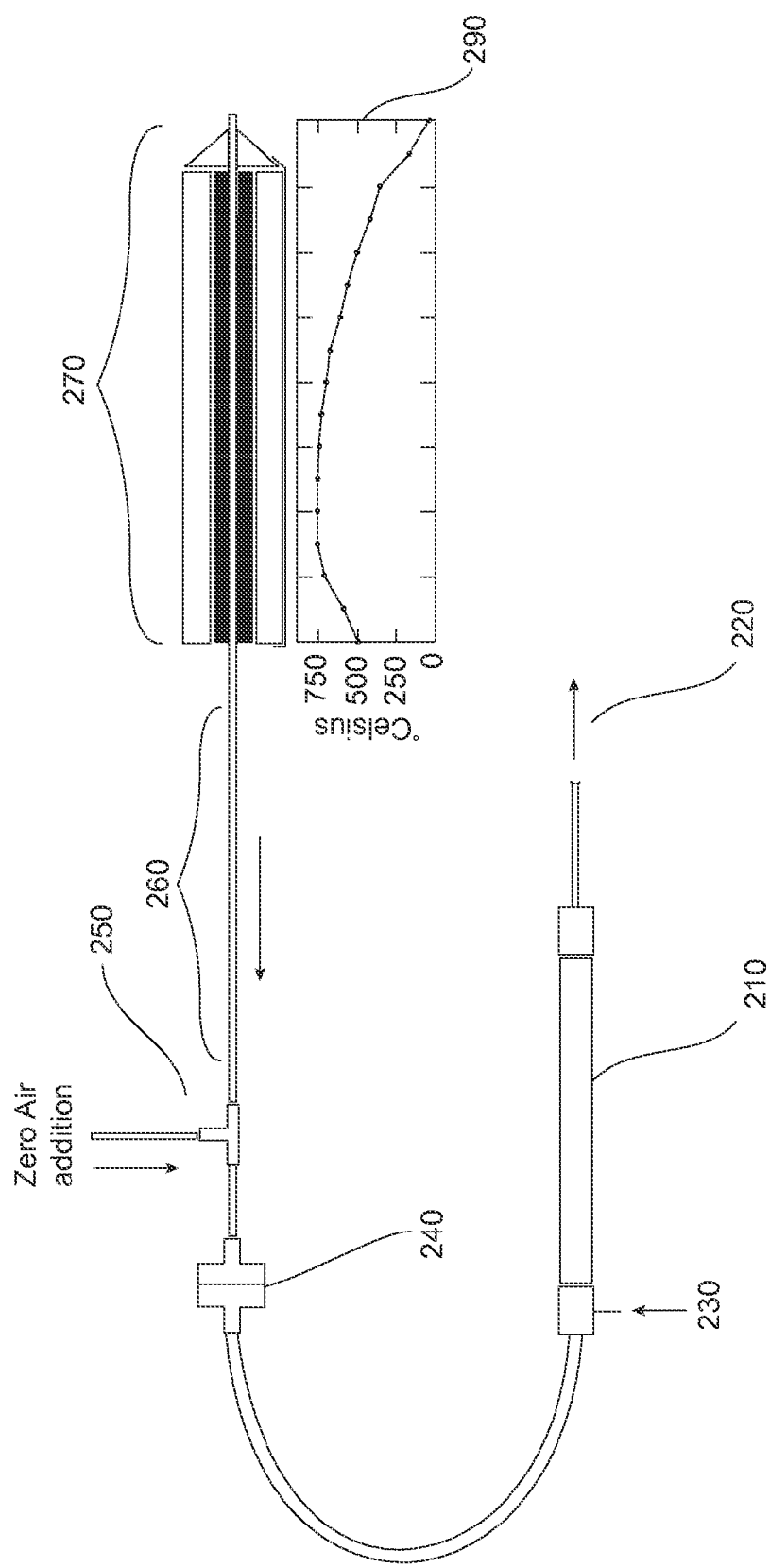
FIG. 2 depicts a conceptual drawing of the $NO_y$ converter and associated components as connected to the optical cavity.
Figure 3A:
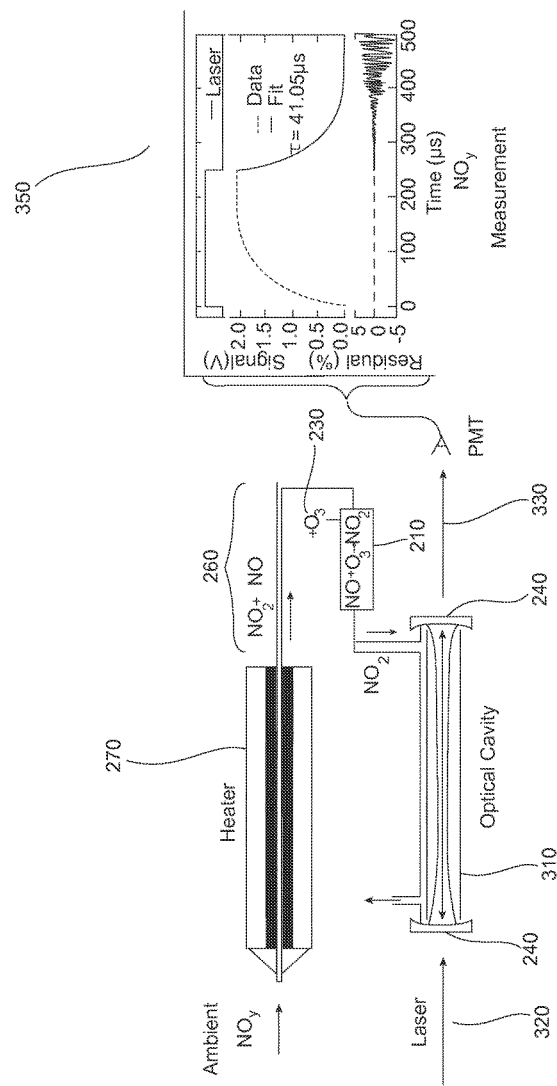
FIG. 3A is an expanded conceptual drawing of the $NO_y$ converter of FIG. 2 showing the optical cavity for the first channel of the measurement system.

FIG. 2 depicts a conceptual drawing of the $NO_y$ converter and associated components as connected to the optical cavity for one of the four channels of the apparatus of FIG. 1. The remaining three channels will be described in more detail below. The other channels use similar components as the $NO_y$ channel, however with fewer components. The thermal heater 270 described in FIGS. 2 and 3A is only required for the $NO_y$ channel, but not for the $O_3$, NO, or $NO_2$ channels. The reactor 210 is not required for the $NO_2$ channel. For the sake of brevity, the same reference numerals are used to describe common components for each channel, as each channel contains the same or similar core components.

For the $NO_y$ channel, an atmospheric sample is obtained through the inlet of heater 270. $NO_y$ and its components are first converted in the $NO_y$ heater 270 into $NO_2$ by thermal decomposition (TD). The heated section 270 comprises a nichrome wire wrapped around a quartz tube. It is thermally insulated with fiberglass insulation and encased in a metal shell ending in a cone, protecting the quartz and conducting heat to the tip. A profile of air temperature as a function of position inside the heater 290 with a flow of 1.5 standard liters per minute at atmospheric pressure is shown in FIG. 2 (with set point higher than normal operation). The total residence time in the heated section is about 48 ms.

The metal shell of heated section 270 ends in a cone-shaped inlet nozzle to ensure that the quartz is heated to the inlet end in order to minimize losses of $HNO_3$, which can be significant on colder surfaces, especially quartz. After the heated section 270, $NO_y$ components have been converted to $NO_2$ (and possibly some NO), which can be transported to the CRDS measurement cell through an arbitrary length of Teflon tubing without significant losses. A cooling region 260 may cool the converted sample, and particle filter 240 may remove large particle impurities from the converted sample.

Zero air addition 250 is used for a periodic measurement of $\tau_0$ to calibrate, or more precisely, zero the device. Periodically (on the order of minutes) during operation, zero air 250 from an air source having no NO components, is fed into the system and the resultant value from the photomultiplier tube (PMT) measured by the data acquisition system. This value then represents the "zero" level of $NO_2$ and is then used as a baseline for subsequent measurements. Frequent calibration or zeroing insures that subsequent measurements are accurate and compensates for drift or other deviations in the measuring system, due to variations in the operation of the photomultiplier tubes, instruments, or even mirror degradation. The required frequency would depend on operational environment. Zeros may be run as infrequently as every 30 minutes, and it may be done as infrequently as every hour if desired.

To zero the instrument (i.e. measure To in equation 1) the inlets are overflowed with zero air 250 generated in situ (or supplied by a cylinder when necessary). Zero air 250 may be generated, for example, by pumping filtered ambient air through a $NO_x$ and $O_3$ scrubber. Overflow is achieved using an annular inlet (i.e. with zero air added through a large diameter tube that surrounds and extends just beyond the sample inlet) for the NO, $NO_2$, and $O_3$ channels, and a simple tee fitting 250, as shown in FIG. 2, is used for the separate $NO_y$ inlet. The overflow during the zeros creates a pressure change of <0.2 hPa (0.03%) for the annular inlet, and a change of 4 hPa (0.5%) in the $NO_y$ inlet.

The change in pressure for the $NO_y$ zero changes the Rayleigh scattering of the air sample, requiring a correction of approximately 60 pptv equivalent $NO_2$, which is based on well-known Rayleigh cross sections and is accurate to well within 3 pptv. Each channel is zeroed approximately every 7 minutes during mobile platform operations, but this time may be increased to 15 to 30 minutes or longer for stationary settings. A zeroing may take on the order of between 10 and 30 seconds, depending on the length of the inlet.

As illustrated in FIG. 2, just prior to a sample entering the optical cavity, excess $O_3$ 230 is added to convert any NO to $NO_2$ in reactor 210. As a result, all of the $NO_y$ components have been converted to $NO_2$ 220 and the resultant measured $NO_2$ provides an indicia of the overall $NO_y$, in one channel of the system. Other channels measure the amount of $NO_2$ or $NO_x$. Subtraction of $NO_x$ from $NO_y$ provides $NO_z$, if desired.

During normal operations, the front half of a quartz tube (heater 270) is heated such that the sample air reaches a temperature of approximately 700° C. The inset 290 in FIG. 2 illustrates a typical temperature profile of the gas in heater 270 (set to heat the gas to 750° C.), measured by insertion of a thermocouple probe in the gas flow during ambient air sampling. As illustrated in the inset 290, the actual sample temperature varies as the air sample flows through heater 270. In practice, heater 270 is set to substantially 750° C. Decomposition of the reactive nitrogen $NO_y$ into $NO_x$ occurs between approximately 650° C. and 750° C. Other temperature values may be used within the spirit and scope of the present invention, provided that the temperature used breaks down the $NO_y$ into $NO_x$ so that it can be measured. For a 1.5 slpm flow, the plug flow residence time in the heated section 270 is approximately 48 ms. The Reynolds number is <1000 for the given range of temperatures, well in the laminar flow regime.

Since the converter 270 itself functions as the inlet, particulate sampling operates with a high efficiency and includes particulate nitrate in the $NO_y$ budget. See, e.g., Rollins, A. W.; Smith, J. D.; Wilson, K. R.; Cohen, R. C. *Real Time In Situ Detection of Organic Nitrates in Atmospheric Aerosols*, Environmental Science & Technology 2010, 5540-5545, incorporated herein by reference.

Particulate nitrate entering the converter 270 should evaporate rapidly, eliminating inertial loss normally associated with particulate sampling. The thermal conversion process produces mainly $NO_2$, although some compounds, such as HONO, may dissociate to NO. A small fraction of the $NO_2$ may also be reduced to NO by reaction with atomic oxygen in the converter. Finally, the thermal converter is not designed to convert NO to $NO_2$. Any NO in the air sample after the heating and cooling process is converted to $NO_2$ via addition of excess $O_3$ 230 just prior to the CRDS measurement cell (in reactor 210), as in the $NO_x$ channel.

The $O_3$ 230 may be generated from the same Pen-Ray lamp source and split evenly between the two channels ($NO_y$ and $NO_y$) using a pair of critical orifices to divide the flow.

FIG. 3A is an expanded conceptual drawing of the $NO_y$ converter of FIG. 2 showing the optical cavity and measurement system. $NO_2$ from reactor 210 is fed to optical cavity 310. To increase stability and compactness over previous designs, the distance between cavity mirrors 240 in optical cavity 310 has been reduced from 1 m to 50 cm. Cavity mirrors 240 with 1 m radius of curvature are reused, and have found to have minimal loss of sensitivity. The corresponding ring down time constant ($\tau_0$), determined by a combination of mirror reflectivity and Rayleigh scattering losses at ambient pressure, is approximately 30 μs, with a precision (1σ, 1 s) of 6 ns.

As noted above with regard to equation (1), a Faraday optical isolator provides protection from optical feedback into the laser. When the light is modulated off, the intensity inside the optical cavities decreases exponentially as measured by photomultiplier tube (PMT) that detects the light intensity transmitted through the rear mirror. The signal from photomultiplier tube PMT is fed to a data acquisition system 350 which may include a digitizer, such as the National Instruments M-series multifunction DAQ, manufactured by National Instruments, of Austin, Tex. Data acquisition system 350 may also include a personal computer, laptop or other computer device known in the art, capable of receiving digitized data from the digitizer, and storing, manipulating, and displaying data results.

The embodiments of FIGS. 2 and 3A illustrate all of the components of one channel of the apparatus of the present invention, namely the $NO_y$ channel. This instrument may be used in a stand-alone mode, or in a four-channel embodiment to measure $O_3$, $NO_y$, $NO_2$, and $NO_y$. In one preferred embodiment, four channels are provided, to measure $O_3$, $NO_y$, $NO_2$, and $NO_y$ using the same 405 nm laser. All four channels use measurement of $NO_2$ to infer or calculate levels of $O_3$, $NO_x$, $NO_2$, and $NO_y$. The same laser, suitably divided, may be used for all four channels, or separate lasers provided. Using a single laser may be preferable, as the same frequency of light is assured between channels. A single cavity ring-down spectrometer (CRDS), suitably plumbed, may sequentially take measurements for all four channels. In the preferred embodiment, separate cavity ring-down spectrometers are provided for each channel. Note that for the sake of clarity, the zero air addition of FIG. 2 is not illustrated in FIGS. 3A-D. However, such a zero air addition may be provided for all four channels, in order to zero or calibrate the devices.

Figure 3B:
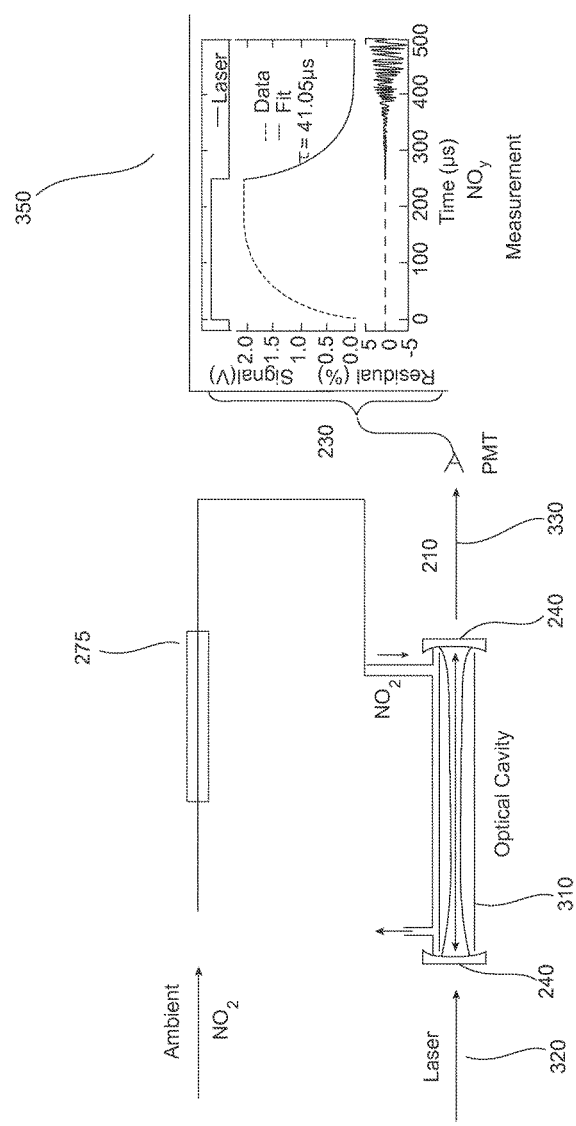
FIG. 3B is a diagram illustrating the main components of the $NO_2$ channel of the measurement system.
Figure 3C:
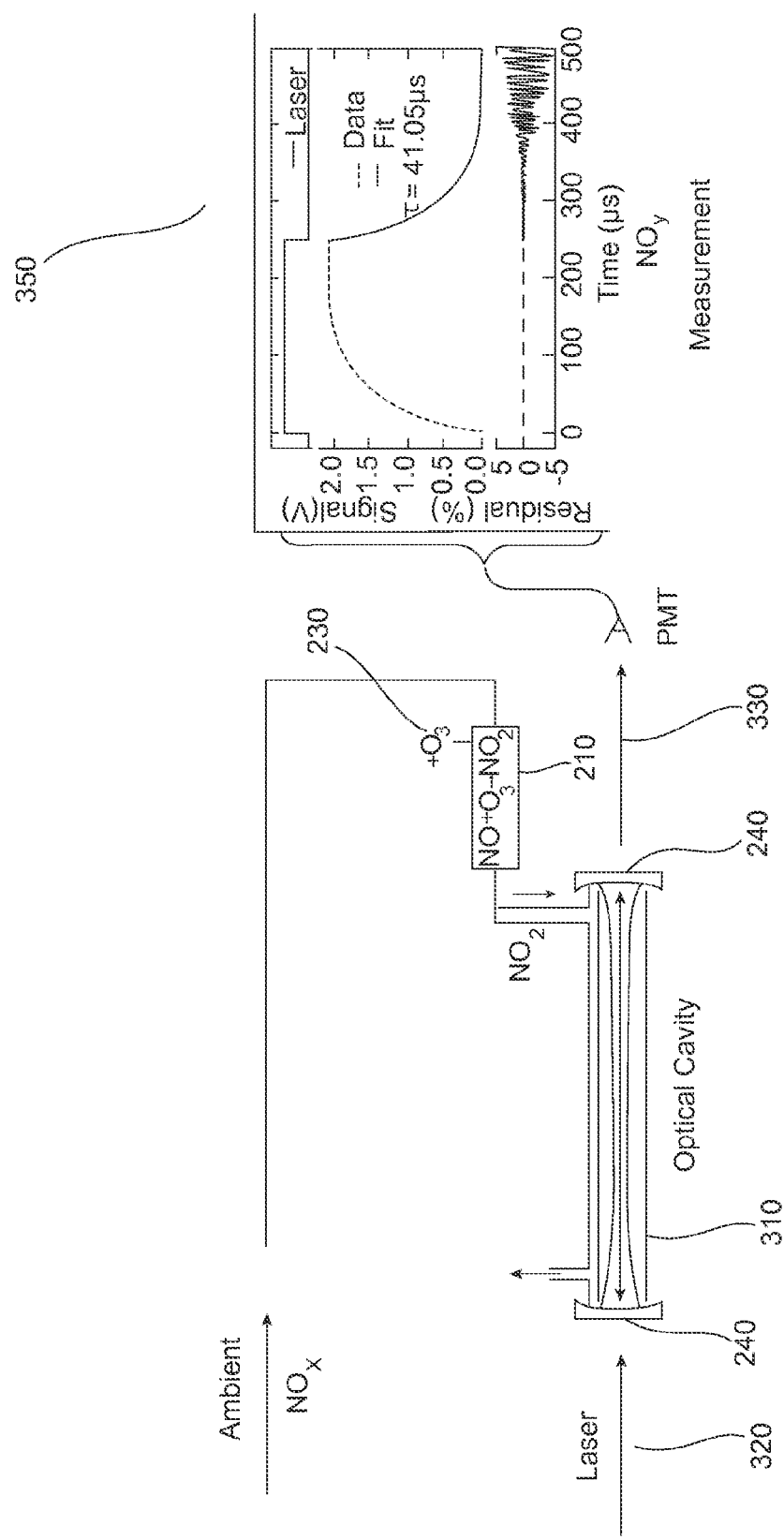
FIG. 3C is a diagram illustrating the main components of the NO (and $NO_y$) channel of the measurement system.
Figure 3D:
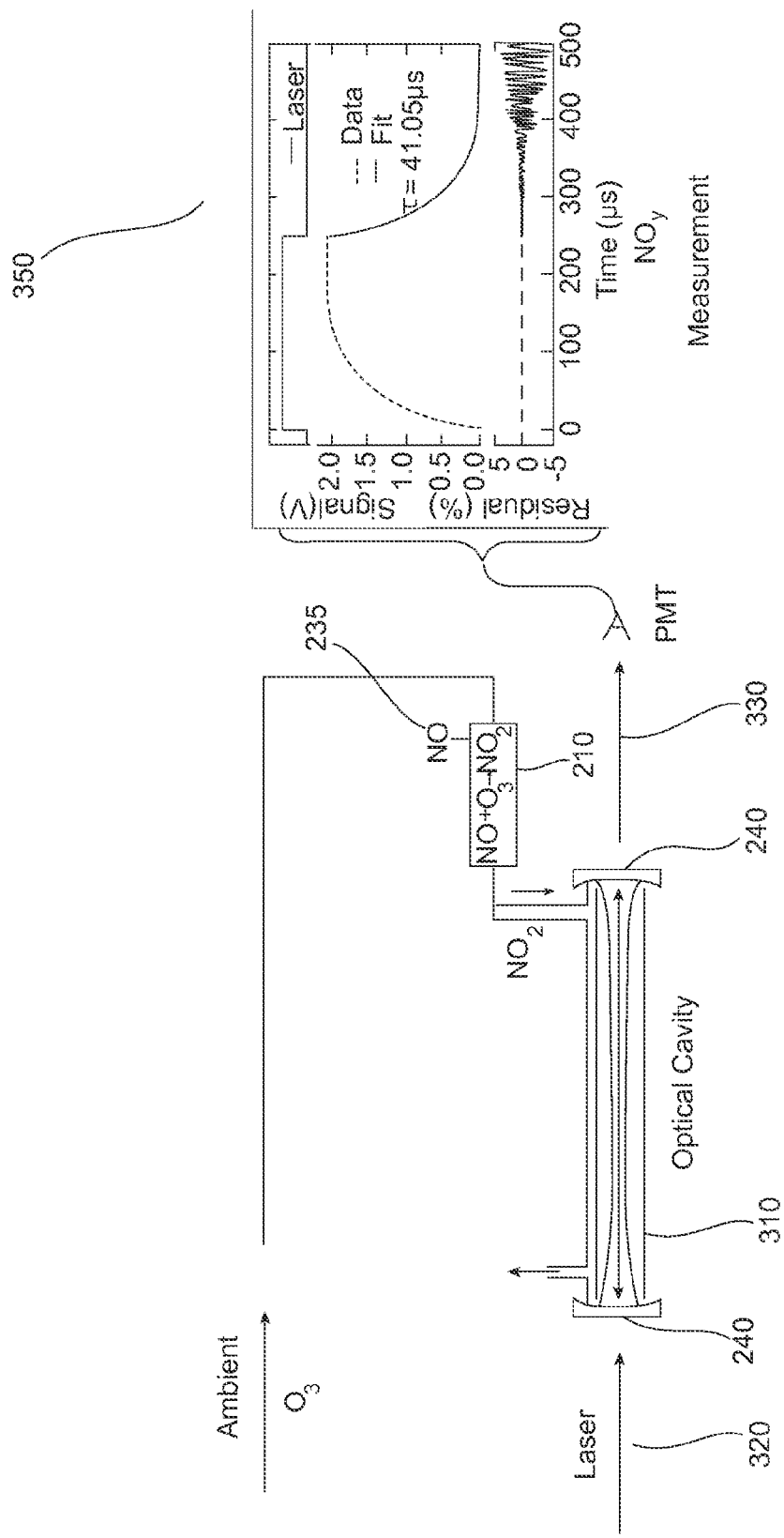
FIG. 3D is a diagram illustrating the main components of the $O_3$ channel of the measurement system.

FIGS. 2 and 3A illustrate all of the components of the $NO_y$ channel. The other three channels contain fewer components and are illustrated in FIGS. 3B-3D. These channels will be described below in terms of the components used in those channels, which, having the same or similar components, may use the same reference numerals.

FIG. 3B is a diagram illustrating the main components of the $NO_2$ channel. The $NO_2$ channel is relatively straightforward. Heater 270 is not used for the $NO_2$ channel, nor is reactor 230. An atmospheric sample is acquired and a "blank volume" 275 is used to provide the same residual time as the other channels, as the $NO_2$ channel does not use a reactor vessel as with the other channels or a heater as with the $NO_y$ channel. The $NO_2$ channel essentially comprises the optical cavity 310 and a suitable blank volume of tubing to emulate the amount of plumbing in the other channels. The ambient $NO_2$ from the atmospheric sample may then be measured by a cavity ring-down spectrometer (CRDS) in optical cavity 310 using photo multiplier tube PMT. The resultant measurement stored in data acquisition system 350 will be proportional to the amount of ambient $NO_2$ in the atmospheric sample. This value may be used by itself, in atmospheric science studies, but may also be used to determine the baseline amount of ambient $NO_2$ to subtract this value out from other channel data as will be discussed below.

FIG. 3C is a diagram illustrating the main components of the NO (and $NO_y$) channel. For the NO (and $NO_y$) channel, heater 270 is not used but reactor 210 is. The NO (and $NO_y$) channel reacts an atmospheric sample with a supply of $O_3$ 230 in a reactor vessel 210. The resultant reaction combines the ambient NO with the $O_3$ 230 in reactor vessel 210 to form $NO_2$. The resultant sample now has both ambient $NO_2$ along with $NO_2$ converted from NO. Since the amount of NO in the original sample has been converted to a similar amount of $NO_2$, measuring the overall $NO_2$ will provide a measurement of NO along with ambient $NO_2$. This combined sample may then be measured by a cavity ring-down spectrometer (CRDS) 310. The resultant measurement will be proportional to the amount of NO and ambient $NO_2$ in the atmospheric sample, which yields the value for $NO_x$. Since the amount of ambient $NO_2$ is measured by the $NO_2$ channel, this value can be subtracted out by the data acquisition system 350, thus yielding a measurement of NO in the atmospheric sample as well.

FIG. 3D is a diagram illustrating the main components of the $O_3$ channel. The $O_3$ channel reacts an atmospheric sample with a supply of NO 235 in a reactor vessel 230. Instead of adding $O_3$ 230, as illustrated in FIGS. 2 and 3, NO 235 is added to the sample to react with the ambient $O_3$. Note that this is the reverse of how the NO channel operates, where $O_3$ is added to the NO, however the reaction is the same. The resultant reaction combines the ambient $O_3$ in the vessel 210 with NO to form $NO_2$, which then may be measured by a cavity ring-down spectrometer (CRDS) 310. The resultant measurement will be proportional to the amount of $O_3$ and ambient $NO_2$ in the atmospheric sample. Since the amount of ambient $NO_2$ is measured by the $NO_2$ channel, this value can be subtracted out by the data acquisition system 350, thus yielding a measurement of $O_3$ in the atmospheric sample.

The $NO_y$ channel of FIG. 3A uses all of the components of FIGS. 2 and 3. The $NO_y$ channel first decomposes all reactive nitrogen compounds in the atmospheric sample in a substantially 650° C. to 750° C. quartz oven 270, as described above. In the oven 270, the $NO_y$ breaks down into NO and $NO_2$. The sample containing the combined NO and $NO_2$ is then fed into a reactor 210, where, as in the NO channel, the NO in the sample reacts with a supply of $O_3$ 230 in the reactor vessel 210. The resultant reaction converts the ambient NO in the vessel to $NO_2$. The amount of NO and $NO_2$ in the decomposed sample will be proportional to the amount of $NO_y$, and since the NO has been converted to a similar amount of $NO_2$, measuring the overall $NO_2$ will provide a measurement of overall $NO_y$. The decomposed and reacted sample may then be measured by a cavity ring-down spectrometer (CRDS) 310. The resultant measurement will be proportional to the amount of $NO_y$ in the atmospheric sample. Since the amount of ambient $NO_2$ is measured by the $NO_2$ channel and the amount of NO and $NO_x$ is measured by the NO channel, other values, such as $NO_z$ can be calculated ($NO_y$—$NO_x$) by the data acquisition system 350.

By using the same reaction of $O_3$ and NO, three of the four channels can measure different atmospheric components using the same or similar hardware. With the addition of the heater 270, $NO_y$ can be measured as proportion to the resultant $NO_2$ after decomposition and reaction. Thus, the present invention provides measurement of the four basic compounds of interest to atmospheric scientists ($O_3$, $NO_y$, $NO_2$, and $NO_y$) with improved accuracy, in a robust and compact instrument. Since the four channels use the same basic cavity ring-down spectrometer (CRDS) 310 and three of the channels use the same (or similar) reactor 210, there is an economy of components and a symmetry in the measuring system which helps insure accurate measurement and simplifies construction and maintenance.

Figure 4:
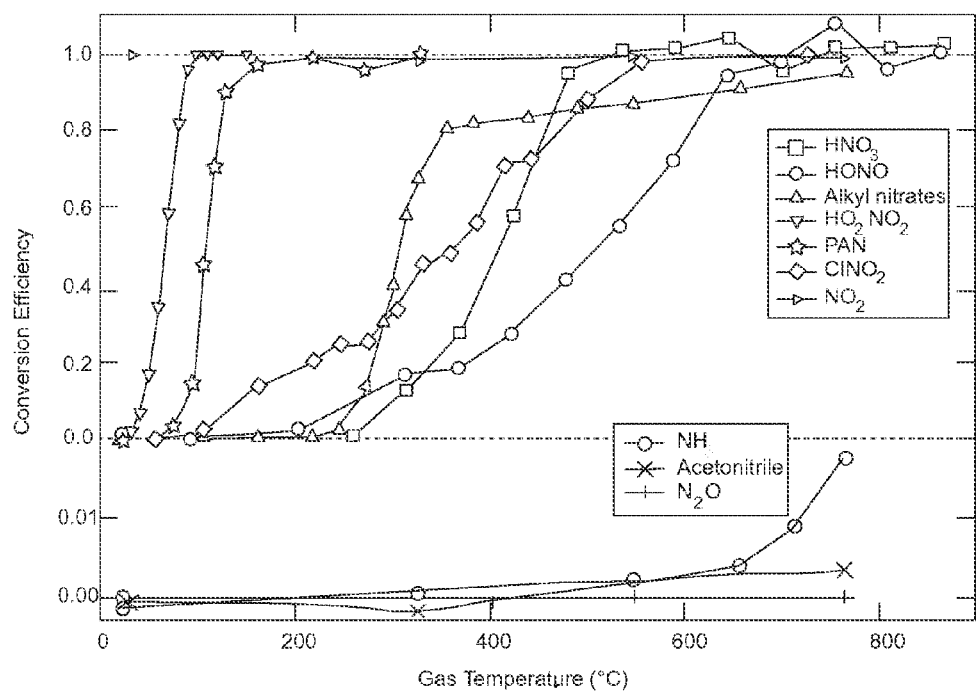
FIG. 4 is a graph where the upper plot shows temperature profiles of several of the most abundant components of $NO_y$, $HNO_3$, and alkyl nitrates compared to a known standard, and the other compounds are scaled to unity at high temperature, and where the lower plot shows temperature profiles from known quantities of possible interference compounds.

FIG. 4 is a graph where the upper plot shows temperature profiles of several of the most abundant components of $NO_y$, $HNO_3$, and alkyl nitrates compared to a known standard, and the other compounds are scaled to unity at high temperature, and where the lower plot shows temperature profiles from known quantities of possible interference compounds. $NH_3$ in dry air resulted in the only measurable interference of <1% at 700° C. The interference was less than 0.1% for air with relative humidity of 10% or greater.

To illustrate the conversion of the various $NO_y$ components, measured temperature profiles of the signal from several $NO_y$ species are shown in FIG. 4. Many of these conversions have been previously demonstrated with heated quartz, as previously discussed, and here, tests have been repeated for the compounds that were readily available. For most samples the output concentration was uncalibrated and scaled to unity in FIG. 4, but a leveling off at high temperature strongly suggests unit conversion. Conversion of $NO_3$ was not explicitly tested, but it is expected that full conversion will take place at operating temperature. See, e.g., Johnston, H. S.; Cantrell, C. A.; Calvert, J. G., *Unimolecular decomposition of $NO_3$ to form NO and $O_2$ and a review of $N_2O_5/NO_3$ kinetics*, Journal of Geophysical Research: Atmospheres 1986, 91, 5159-5172, incorporated herein by reference.

Measurements of $HNO_3$ and PAN were directly compared to that of a heated Mo catalytic converter, and full conversion was achieved at the operating temperature of 700° C. The alkyl nitrates (a mix of methyl, ethyl, i-propyl, n-propyl, i-pentyl, and i-butyl nitrate from a calibration cylinder) show a rapid conversion to $NO_2$ up to 300° C., then a slower increase up to 800° C., where we see full conversion to within the cylinder specifications (±10%). The slower conversion at higher temperature differs from previously reported temperature profiles for organic nitrates, and may be due to the temperature profile specific to the inlet of the present invention. Since the design goal is total rather than speciated $NO_y$, the behavior of organic nitrates at intermediate temperatures does not significantly affect the performance of the total $NO_y$ measurement.

Some nitrogen-containing gases that are not products of $NO_x$ oxidation and therefore not components of $NO_y$ as traditionally defined could conceivably be converted to $NO_x$ at high temperatures. If they are present at mixing ratios comparable to or larger than $NO_y$ in the atmosphere, as can be the case for $NH_3$, $N_2O$ and nitriles, these compounds could represent a significant interference for an $NO_y$ measurement based on thermal conversion to $NO_2$.

Known standards of $NH_3$, $N_2O$, and acetonitrile were sampled with the thermal converter, as shown in the lower plot of FIG. 4. Ammonia resulted in the only non-zero interference, reaching about 1% conversion at our working sample temperature of 700° C. However, this interference was only present in dry air from a cylinder (<1 ppm water vapor mixing ratio). A relative humidity of 10% was enough to suppress the $NH_3$ conversion to $NO_2$ to below 0.1%, such that it can be considered a negligible interference in nearly all field situations.

As with Day et al., cited previously, the apparatus of the present invention is not expected to be sensitive to aromatic nitro compounds. Furthermore, they are not typically expected to be a large fraction of $NO_y$. Reports of particle bound nitro-PAHs in Los Angeles, for example, have an equivalent gas phase 170 concentration <0.1 pptv. See. e.g., Reisen, F.; Arey, J., *Atmospheric Reactions Influence Seasonal PAH and Nitro-PAH Concentrations in the Los Angeles Basin*, Environmental Science & Technology 2005, 39, 64-73, incorporated herein by reference.

Other interferences to $NO_2$ detection using 405 nm CRDS have been described before. A water vapor interference results from the change in Rayleigh scattering, which was measured by Fuchs, et al., cited above, and results in a small correction to the data. Absorbing gases other than $NO_2$, such as α-dicarbonyls, are a direct interference but constitute a small percentage of $NO_x$ in most scenarios. However, since these compounds require a higher dissociation temperature than the $NO_y$ converter provides, they only represent an error in the $NO_2$ baseline.

The subtractive measurements of NO, $O_3$, and $NO_z$(=$NO_y$—$NO_x$) are therefore unaffected by α-dicarbonyls. Direct absorption by ambient $O_3$ in the NO and $NO_2$ channels represents a negligible interference because the absorption cross-section of $O_3$ at 405 nm is $1.5 \times 10^{-23}$ cm2 (~$4 \times 10^4$ times smaller than that of $NO_2$). See, e.g., Axson, J. L.; Washenfelder, R. A.; Kahan, T. F.; Young, C. J.; Vaida, V.; Brown, S. S., *Absolute ozone absorption cross section in the Huggins Chappuis minimum (350-470 nm) at 296 K*, Atmospheric Chemistry and Physics 2011, 11, 11581-11590, incorporated herein by reference.

For 50 ppbv (parts per billion, volume) of $O_3$, the optical extinction is $1:9 \times 10^{-11}$ cm$^{-1}$, or equivalent to approximately 1 pptv of $NO_2$. The optical extinction due to the added 30 ppmv $O_3$ in the $NO_x$ and $NO_y$ channels is measurable, but this signal is constant across instrument zeros and thus does not contribute to the measurement. However, it provides a convenient means to measure the added $O_3$ by switching the $O_3$ addition on and off during periods of zero air sampling.

Figure 5:
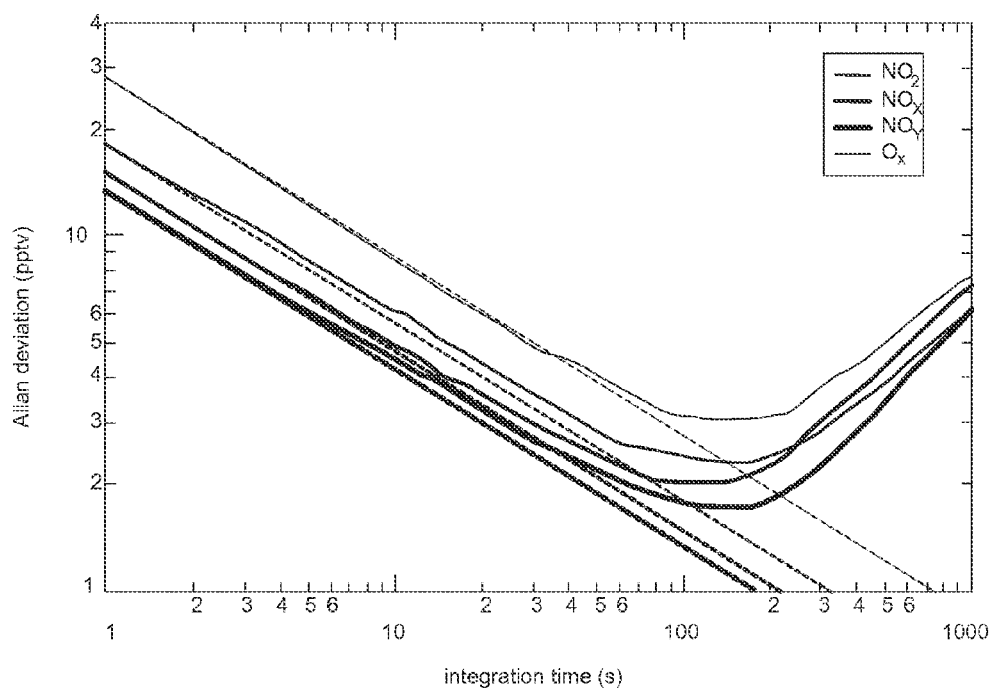
FIG. 5 is a graph illustrating the dependence of 1σ precision on integration time (Allan deviation plots) for the four channels measuring $NO_2$ in zero air under laboratory conditions. The dashed lines show the expected trend for statistically random noise.

FIG. 5 is a graph illustrating the dependence of 1σ precision on integration time (Allan deviation plots) for the four channels measuring $NO_2$ in zero air under laboratory conditions. The dashed lines show the expected trend for statistically random noise. The $NO_2$ calibrations for the four channels have also been described by Washenfelder and Fuchs, cited previously. $O_3$ may be measured by a commercial UV absorption $O_3$ instrument and then quantitatively converted to $NO_2$ in excess NO. The $NO_2$ is then measured by CRDS in the four channels.

The system of the present invention thus provides four measurements (channels) of the effective absorption cross-section, $\sigma_{NO2}$, which differ by less than 2% between the channels. The day-to-day variability of these measurements is less than 1%. FIG. 5 shows a typical plot showing the relation between integration time and 1σ precision (Allan deviation plot) for the four channels during sampling of zero air. The dashed lines indicate the expected square root relationship for statistically random noise. All channels follow a nearly statistical noise distribution out to 100 s integration time, resulting in a maximum sensitivity of a few pptv (parts per trillion per volume). Any uncertainties of the $NO_2$ measurement in the four channels may be due to calibration uncertainties and result in a 3% uncertainty in the base measurement. Conversion of $NO_2$ to $N_2O5$ in the two channels that add excess $O_3$ ($NO_x$ and $NO_y$) increases the uncertainty of $NO_x$ measurements up to 5%.

The uncertainty of the $NO_y$ measurement must include the conversion efficiency uncertainties for the different $NO_y$ compounds. The comparisons to known concentrations ($HNO_3$, PAN, and alkyl nitrates) showed full conversion to within the uncertainty of the standards (approximately 10%, from the uncertainty in conversion efficiency of the Mo converter and the alkyl nitrate cylinder mixing ratio). But for the other compounds quantitative conversion was implied by the temperature profile and uncertainties are unavailable. A total uncertainty was derived empirically by comparison of the thermal dissociation CRDS instrument to a standard $NO_y$ instrument under field conditions. The results of this comparison, discussed below, suggest a limiting uncertainty in the $NO_y$ measurement of 12%.

The new $NO_y$ detection method and apparatus of the present invention was quantitatively tested during two field comparisons in 2013. One was the Uintah Basin Winter Ozone Study (UBWOS) 2013, during which measurements from the present invention were compared to the sum of the separately measured $NO_y$ components. The other comparison occurred during the Southeast Oxidant and Aerosol Study (SOAS), where total $NO_y$ measurement from the present invention was directly compared to total $NO_y$ measured with a standard Mo catalytic converter.

Figure 6:
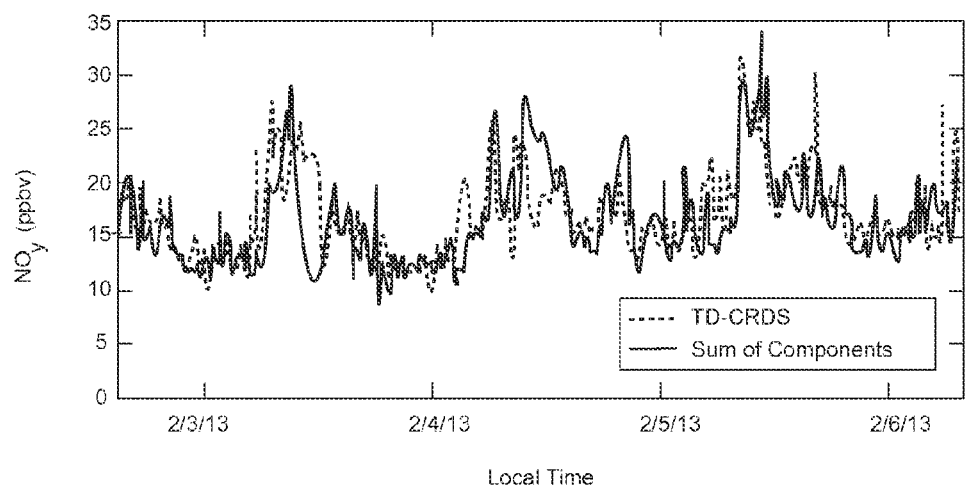
FIG. 6 is a representative time series showing several days of measurement comparing the total $NO_y$ as measured by the instrument of the present invention with the sum of $NO_y$ components during a February/March UBWOS field campaign, during which $NO_x$ contributed 28% to $NO_y$.
Figure 7:
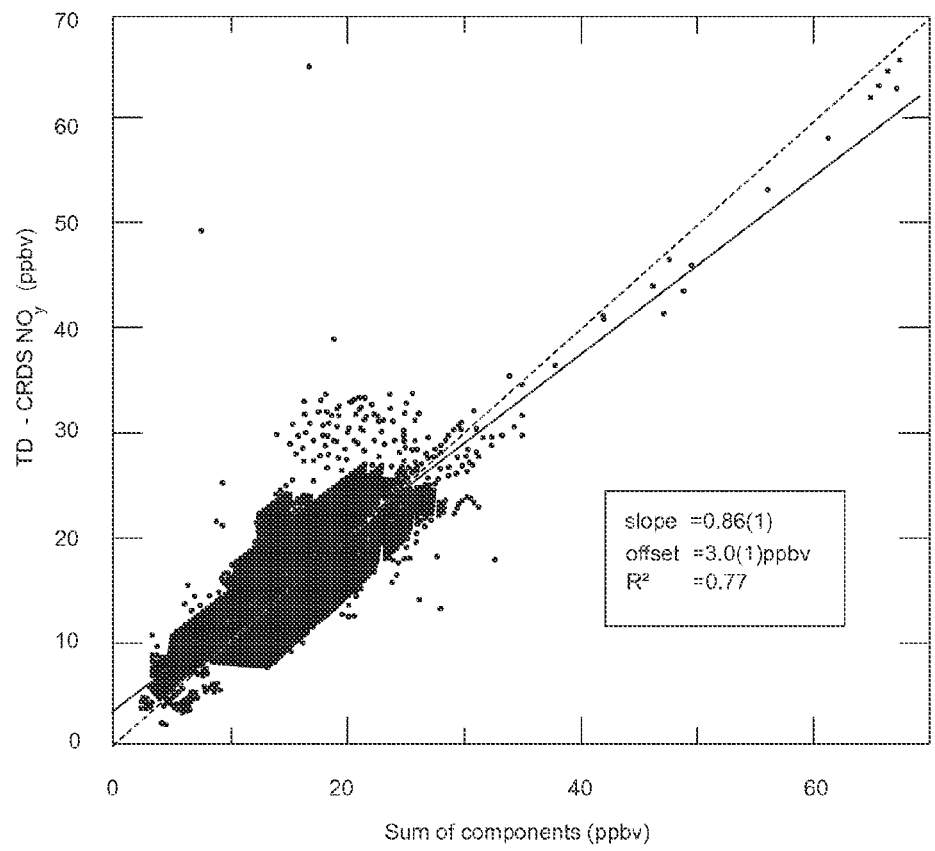
FIG. 7 is a correlation plot of $NO_y$ to the sum of components for the entire campaign.
Figure 8:
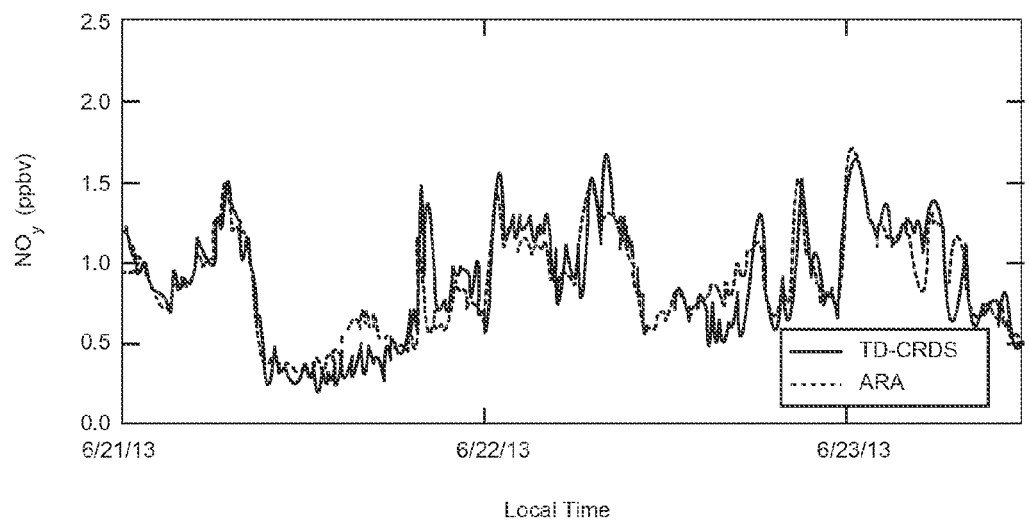
FIG. 8 is a time series comparing the total $NO_y$ measured by TD to total $NO_y$ measured by a Mo catalytic converter during the June/July SOAS field campaign, during which $NO_x$ contributed 43% to $NO_y$.
Figure 9:
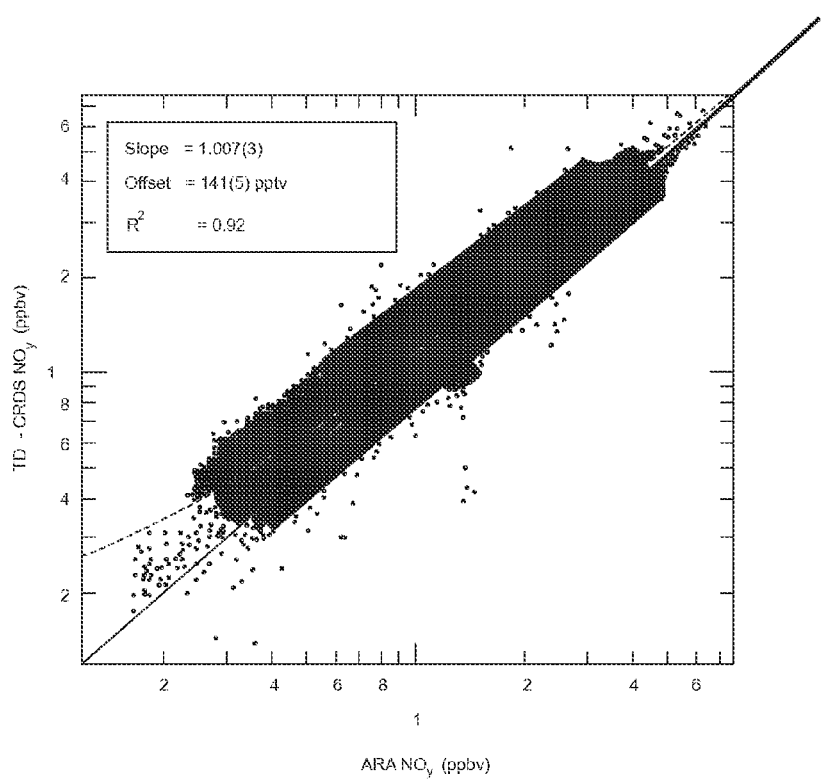
FIG. 9 is a correlation plot for the two methods for the entire campaign.

FIG. 6 is a representative time series showing several days of measurement comparing the total $NO_y$ as measured by the instrument of the present invention with the sum of $NO_y$ components during a February/March UBWOS field campaign, during which NO contributed 28% to $NO_y$. FIG. 7 is a correlation plot of $NO_y$ to the sum of components for the entire campaign. FIG. 8 is a time series comparing the total $NO_y$ measured by TD to total $NO_y$ measured by a Mo catalytic converter during the June/July SOAS field campaign, during which $NO_x$ contributed 43% to $NO_y$. FIG. 9 is a correlation plot for the two methods for the entire campaign. All data shown are five minute averages.

The UBWOS 2013 campaign was a 4-week study in the Uintah Basin of Utah in February and March. The area is host to extensive oil and gas operations, and regularly experiences strong temperature inversions. This results in very high ozone events as well as elevated levels of $NO_z$ ($\equiv NO_y - NO_x$, averaging about 12 ppbv over the campaign), making it an ideal field test for the $NO_y$ converter.

In addition to measurement of total $NO_y$ and $NO_x$, two chemical ionization mass spectrometers measured concentrations of $HNO_3$, $Cl\ NO_2$, $HONO$, and PAN. See, e.g., Slusher, D. L.; Huey, L. G.; Tanner, D. J.; Flocke, F. M.; Roberts, J. M., *A thermal dissociation-chemical ionization mass spectrometry (TD-CIMS) technique for the simultaneous measurement of peroxyacyl nitrates and dinitrogen pentoxide*, Journal of Geophysical Research: Atmospheres 2004, 109, and Roberts, J. M.; Veres, P.; Warneke, C.; Neuman, J. A.; Washenfelder, R. A.; Brown, S. S.; Baasandorj, M.; Burkholder, J. B.; Burling, I. R.; Johnson, T. J.; Yokelson, R. J.; de Gouw, J., *Measurement of HONO, HNCO, and other inorganic acids by negative-ion proton-transfer chemical-ionization mass spectrometry (NI-PT-CIMS): application to biomass burning emissions*, Atmospheric Measurement Techniques 2010, 981-990, both of which are incorporated herein by reference. A particle-into-liquid sampler measured particle phase inorganic nitrate, and a separate cavity ring-down system measured $NO_3$ and $N_2O_5$.

FIGS. 6 and 7 illustrate the comparison between total $NO_y$ measurement and the sum of the $NO_y$ components as measured by different instruments (not including organic nitrates), for which $NO_x$ represents a 28% contribution to $NO_y$. FIG. 6 shows a representative time series over a few days.

FIG. 7 plots the correlation between the $NO_y$ measurement and the sum of the components over the whole campaign. The data presented are 5-minute averages because inlets had small differences in location (several meters separation) at the field site, and because of frequent transient high $NO_x$ spikes that were inhomogeneously mixed. On average, the new NO instrument measured 0.9 ppbv (6%) higher $NO_y$ than the sum of components. This difference may be due to organic nitrates, for which data are not available in 2013, or simply from the combined uncertainties of the individual measurements.

The SOAS campaign was a 6-week study in central Alabama in June and July of 2013. The site is co-located with a SEARCH network monitoring station maintained by Atmospheric Research and Analysis, Inc. (ARA), which collects long-term measurements of a suite of gases, including total $NO_y$. The ARA $NO_y$ measurement is performed using a standard Mo catalytic converter that converts $NO_y$ to NO, followed by chemiluminescent detection of NO. The SOAS campaign thus provided an opportunity for direct comparison between 250 the TD-CRDS $NO_y$ and a more conventional $NO_y$ instrument. The inlets were separated by about 110 meters horizontally and 15 meters vertically, with the ARA inlet positioned a few meters above ground. Although mirror purge volumes were also not used for this campaign, a hydrocarbon scrubber as in the UBWOS campaign was not required.

However, the high humidity of air sampled during summertime in Alabama required drying the sample air with a cold trap for all the channels (after the converter for the $NO_y$ channel) in order to avoid signal degradation due to water vapor condensation on the mirrors. This modification is similar to that used on commercial CRDS instruments that measure $NO_2$ alone. The cold trap reduced the relative humidity to <15%, but did not measurably influence the transmission of $NO_2$.

FIGS. 8 and 9 illustrate a comparison of the two measurements. In this case the average $NO_x$ contribution to $NO_y$ was 43% during the campaign. High concentration spikes tended to show poorer agreement, most likely due to the separation between the inlets. FIG. 8 plots a time series of the two instruments spanning two days with low occurrences of large concentration spikes. FIG. 9 is a correlation plot of all the data from the campaign. The slope is equal to unity to within a 5% measurement uncertainty, but there is an average offset of about 140 pptv. This offset may be caused by variation in the sensitivity to specific components of $NO_y$, such as coarse aerosol nitrate, between the two instruments, a real difference in ambient $NO_y$ due to the separation of the inlets, a systematic error between the two instruments, or a combination of these. Nevertheless, the observed offset provides an upper limit estimate for our $NO_y$ measurement uncertainty (12%) relative to an accepted standard measurement method.

Thus, applicants have developed a new and useful, compact and robust CRDS instrument measuring NO, $NO_2$, $O_3$, and total $NO_y$. Applicant has further demonstrated a new technique for measuring $NO_y$ using thermal decomposition to $NO_2$ in a heated quartz inlet, followed by conversion of NO to $NO_2$ in excess $O_3$. Temperature profiles of individual components are consistent with unit conversion efficiency for every $NO_y$ component measured, and there are no significant interferences from other reduced nitrogen compounds. Instrument performance has been demonstrated with comparisons at two ground sites. These field tests show agreement both with the sum of $NO_y$ components measured by separate, independent instruments, and with a measurement of total $NO_y$ by a standard molybdenum catalytic converter to within <1% and an absolute offset of 140 pptv. The latter comparison allows for an empirical definition of an upper limit on the $NO_y$ measurement uncertainty of 12%, although the uncertainty may depend on the relative concentrations of $NO_y$ components. The instrument performance was equivalent while sampling from within a moving vehicle (instrumented van), and has been recently demonstrated from aircraft such as the National Science Foundation C-130 (February-March 2015) and the NOAA P-3 Orion.

While the preferred embodiment and various alternative embodiments of the invention have been disclosed and described in detail herein, it may be apparent to those skilled in the art that various changes in form and detail may be made therein without departing from the spirit and scope thereof.

For example, methods may be provided to prevent mirror degradation without the need for drying the sample air or scrubbing it of hydrocarbons. Applicant is currently testing designs using smaller purge volumes that require smaller path length corrections than in previously reported instruments, as well as testing other methods to make the mirrors less susceptible to condensation effects. The present invention, while smaller than previously reported versions, can be further reduced in size to allow for more versatile deployments on mobile platforms.

We claim:

1. A multi-channel instrument for simultaneously measuring at least reactive nitrogen ($NO_y$) content, nitrogen dioxide content, ambient nitrogen oxides ($NO_x$=NO+$NO_2$)) content and ozone content in gas samples, the multi-channel instrument comprising:

a laser producing a primary laser beam;
beam divider coupled to the laser, dividing the primary laser beam into at least a first laser beam, a second laser beam, a third laser beam, and a fourth laser beam;
a first channel measuring reactive nitrogen ($NO_y$) content, the first channel comprising:
  a heater receiving a first gas sample, the heater heating the first gas sample and decomposing reactive nitrogen in the first gas sample into nitrogen oxides to output a decomposed first gas sample;
  a first reactor, coupled to the heater and an ozone supply, receiving the decomposed first gas sample and ozone and reacting nitrogen oxide in the decomposed first gas sample into nitrogen dioxide to produce a decomposed and reacted first gas sample; and
  a first cavity ring-down spectrometer, coupled to the first reactor and receiving the decomposed and reacted first gas sample, measuring the nitrogen dioxide content of the decomposed reacted first gas sample, and outputting a first output signal proportional to the nitrogen dioxide content in the decomposed reacted first gas sample, the first cavity ring-down spectrometer comprising a first optical cavity coupled to the beam divider and receiving the first laser beam, the first laser beam traversing the first optical cavity, such that when the laser is turned off, measurement is made of time for light from the first laser beam to decay to 1/e of its initial intensity to calculate concentration of the nitrogen dioxide in the first optical cavity, wherein the nitrogen dioxide content in the decomposed reacted first gas sample is proportional to the reactive nitrogen content ($NO_y$) in the first gas sample and the first output signal is proportional to the total reactive nitrogen content ($NO_y$) in the first gas sample;
a second channel, measuring nitrogen dioxide content, the second channel comprising:
  a second cavity ring-down spectrometer receiving a second gas sample, the second cavity ring-down spectrometer measuring the nitrogen dioxide content of the second gas sample, and outputting a second output signal proportional to the ambient nitrogen dioxide content in the second gas sample, the second cavity ring-down spectrometer comprising a second optical cavity, coupled to the beam divider and receiving the second laser beam, the second laser beam traversing the second optical cavity, such that when the laser is turned off, measurement is made of time for light from the second laser beam to decay to 1/e of its initial intensity to calculate concentration of the nitrogen dioxide in the second optical cavity, producing the second output signal proportional to the ambient nitrogen dioxide content in the second gas sample;
a third channel, measuring ambient nitrogen oxides ($NO_x$=NO+$NO_2$)) content, the third channel comprising:
  a second reactor, coupled to the ozone supply, the second reactor receiving a third gas sample and ozone and reacting nitric oxide (NO) in the third gas sample into nitrogen dioxide ($NO_2$) to produce reacted third sample; and
  a third cavity ring-down spectrometer, coupled to the second reactor and receiving the reacted third gas sample, measuring the nitrogen dioxide content of the reacted third gas sample, and outputting an output signal proportional to the nitrogen dioxide content in the reacted third gas sample, the second cavity ring-down spectrometer comprising a third optical cavity, coupled to the beam divider and receiving the third laser beam, the third laser beam traversing the third optical cavity, such that when the laser is turned off, measurement is made of time for light from the third laser beam to decay to 1/e of its initial intensity to calculate concentration of the nitrogen dioxide in the third optical cavity, wherein the nitrogen dioxide content in the second reacted gas sample is proportional to the ambient nitrogen oxides ($NO_x$=NO+$NO_2$)) content in the third gas sample and the third output signal is proportional to the ambient nitrogen oxides ($NO_x$) content in the third gas sample; and
a fourth channel measuring ozone content, the fourth channel comprising:
  a third reactor, coupled to a nitric oxide (NO) supply, the third reactor receiving a fourth gas sample and nitric oxide and reacting ozone in the fourth gas sample with nitric oxide into nitrogen dioxide to produce a reacted fourth gas sample; and
  a fourth cavity ring-down spectrometer, coupled to the third reactor and receiving the reacted fourth gas sample, measuring the nitrogen dioxide content of the reacted fourth gas sample, and outputting an output signal proportional to the nitrogen dioxide content in the reacted fourth gas sample, the fourth cavity ring-down spectrometer comprising a fourth optical cavity, coupled to the beam divider and receiving the fourth laser beam, the fourth laser beam traversing the fourth optical cavity, such that when the laser turned off, measurement is made of time for light from the fourth laser beam to decay to 1/e of its initial intensity to calculate concentration of the nitrogen dioxide in the fourth optical cavity, wherein the nitrogen dioxide content in the reacted fourth gas sample is proportional to the ozone content in the fourth gas sample plus the ambient nitrogen dioxide in the fourth gas sample and the output signal is proportional to the ozone content in the fourth gas sample plus the ambient nitrogen dioxide in the fourth gas sample.

2. The instrument of claim 1, further comprising:
a data processing system, receiving the first output signal and calculating reactive nitrogen content in the gas sample as a function of the first output signal.

3. The instrument of claim 2, wherein the first gas sample, the second gas sample, the third gas sample, and the fourth gas sample each comprise an atmospheric air sample, each collected contemporaneously with one another.

4. The instrument of claim 3, wherein the data processing system subtracts the second output signal proportional to measured ambient nitrogen dioxide content value as measured by the second channel from the third output signal proportional to measured ambient nitrogen oxides ($NO_x$) content value as measured by the third channel to calculate nitric oxide (NO) in the gas samples.

5. The instrument of claim 3, wherein the data processing system subtracts second output signal proportional to measured ambient nitrogen oxides ($NO_x$) content value as measured by the second channel from the first output signal proportional to reactive nitrogen content ($NO_y$) value as measured by the first channel, to calculate oxidized reactive nitrogen ($NO_z$) in the gas samples.

6. The instrument of claim 3, wherein the data processing system subtracts the fourth output signal proportional to ozone content value as measured by the fourth channel, from the second output signal proportional to nitrogen dioxide content value as measured by the second channel, to calculate ozone content in the gas samples.

7. The instrument of claim 1, wherein the heater comprises a quartz tube wrapped with nichrome wire.

8. A method of simultaneously measuring at least reactive nitrogen content, nitrogen dioxide content, the ambient nitrogen oxides ($NO_x$=$NO$+$NO_2$) content and ozone content in a gas samples, comprising the steps of:
  generating a laser beam with a laser;
  dividing, in a beam divider coupled to the laser, the primary laser beam into at least a first laser beam, a second laser beam, a third laser beam, and a fourth laser beam;
  measuring reactive nitrogen ($NO_y$) content in a first channel comprising the steps of:
    heating a first gas sample in a heater, to decompose reactive nitrogen in the first gas sample into nitrogen oxides outputting a decomposed first gas sample;
    reacting the decomposed first gas sample with ozone in a first reactor coupled to the heater and an ozone supply, to react nitric oxide in the decomposed first gas sample with the ozone, into nitrogen dioxide to produce a decomposed and reacted first gas sample;
    measuring nitrogen dioxide content in the decomposed and reacted first gas sample in a first cavity ring-down spectrometer coupled to the reactor, the first cavity ring-down spectrometer comprising a first optical cavity coupled to beam divider and receiving the first laser beam, the first laser beam traversing the first optical cavity, such that when the laser is turned off, measurement is made of time for light from the first laser beam to decay to 1/e of its initial intensity to calculate the concentration of the nitrogen oxide in the first optical cavity; and
    outputting from the first cavity ring-down spectrometer, an output signal proportional to the nitrogen dioxide content in the decomposed reacted first gas sample;
    wherein the nitrogen dioxide content in the decomposed reacted first gas sample is proportional to the reactive nitrogen content in the first gas sample and the output signal is proportional to the total reactive nitrogen content in the first gas sample;
  measuring nitrogen dioxide content in a the second channel, comprising the steps of:
    measuring, in a second cavity ring-down spectrometer receiving a second gas sample, the second cavity ring-down spectrometer measuring the nitrogen dioxide content of the second gas sample, and outputting a second output signal proportional to the ambient nitrogen dioxide content second gas sample, the second cavity ring-down spectrometer comprising a second optical cavity, coupled to the beam divider and receiving the second laser beam, the second laser beam traversing the second optical cavity, such that when the laser is turned off, measurement is made of time for light from the second laser beam to decay to 1/e of its initial intensity to calculate concentration of the nitrogen dioxide in the second optical cavity, producing the second output signal proportional to the ambient nitrogen dioxide content in the second gas sample;
  measuring ambient nitrogen oxides ($NO_x$=$NO$+$NO_2$)) content in a third channel, comprising the steps of:
    reacting, in a second reactor receiving a third gas sample, and to the ozone supply, the second reactor receiving the third gas sample and ozone and reacting nitric oxide (NO) in the third gas sample into nitrogen dioxide ($NO_2$) to produce a reacted third gas sample;
    measuring, in a third cavity ring-down spectrometer, coupled to the second reactor and receiving the reacted third gas sample, measuring the nitrogen dioxide content of the reacted third gas sample, and outputting an output signal proportional to the nitrogen dioxide content in the reacted third gas sample, the third cavity ring-down spectrometer comprising a third optical cavity, coupled to the beam divider and receiving the third laser beam, the third laser beam traversing the third optical cavity, such that when the laser turned off, measurement is made of time for light from the third laser beam to decay to 1/e of its initial intensity to calculate concentration of the nitrogen oxide in the third optical cavity, wherein the nitrogen dioxide content in the third gas sample is proportional to the ambient nitrogen oxides ($NO_x$) content in the third gas sample and the third output signal is proportional to the ambient nitrogen oxides ($NO_x$) content in the third gas sample;
  measuring ozone content in a fourth channel, comprising the steps of:
    reacting, in a third reactor receiving a fourth gas sample and to a nitrogen oxide (NO) supply, the third reactor receiving the fourth gas sample and nitrogen oxide and reacting ozone in the fourth gas sample with nitrogen oxide into nitrogen dioxide to produce a reacted fourth gas sample;
    measuring, in a fourth cavity ring-down spectrometer, coupled to the third reactor and receiving the reacted fourth gas sample, measuring the nitrogen dioxide content of the reacted fourth gas sample, and outputting an output signal proportional to the nitrogen dioxide content in the reacted fourth gas sample, the fourth cavity ring-down spectrometer comprising a fourth optical cavity, coupled to the beam divider and receiving the first laser beam, the fourth laser beam traversing the fourth optical cavity, such that when the laser turned off, measurement is made of time for light from the fourth laser beam to decay to 1/e of its initial intensity to calculate concentration of the nitrogen dioxide in the fourth optical cavity, wherein the nitrogen dioxide content in the reacted fourth gas sample is proportional to the ozone content in the fourth gas sample plus the ambient nitrogen dioxide in the fourth gas sample and the output signal is proportional to the ozone content in the fourth gas sample plus the ambient nitrogen dioxide in the fourth gas sample.

9. The method of claim 8, wherein the first gas sample, the second gas sample, the third gas sample, and the fourth gas sample each comprise an atmospheric air sample, each collected contemporaneously with one another.

10. The method of claim 9, wherein the step of heating the first gas sample comprises the step of heating the first gas sample to substantially 650° C. to 750° C. to decompose reactive nitrogen $NO_y$ into nitrogen oxides NO and $NO_2$.

11. The method of claim 10, wherein the heater comprises a quartz tube wrapped with nichrome wire.

12. The method of claim 9, further comprising the steps of:
subtracting, in a data processing system, the second output signal proportional to the measured ambient nitrogen dioxide content value as measured by the second channel from the third output signal proportional to the measured ambient nitrogen oxides ($NO_x$) content value as measured by the third channel to calculate nitrogen oxide (NO) in the gas samples.

13. The method of claim 9, further comprising the steps of:
subtracting in a data processing system, the second output signal proportional to the measured ambient nitrogen oxides ($NO_x$) content value as measured by the second channel from the first output signal proportional to the measured reactive nitrogen content ($NO_y$) in the first gas sample as measured by the first channel to calculate oxidized reactive nitrogen ($NO_z$) in the gas samples.

14. The method of claim 9, further comprising the step of:
subtracting, in a data processing system, the fourth output signal proportional to ozone content value as measured by the fourth channel, from the second output signal proportional to nitrogen dioxide content value as measured by the second channel, to calculate ozone content in the gas samples.

* * * * *